United States Patent
Frenkel et al.

(10) Patent No.: US 9,866,507 B2
(45) Date of Patent: Jan. 9, 2018

(54) METHOD OF MONITORING WELL-BEING OF SEMI-INDEPENDENT PERSONS AND SYSTEM THEREOF

(71) Applicant: AGT INTERNATIONAL GMBH, Zurich (CH)

(72) Inventors: Assaf Frenkel, Ramat Hasharon (IL); Zachi Ekhous, Lapid (IL); Gdalia Lenz, Zikhron Ya'aqov (IL); Yoav Ariav, Kfar Saba (IL); Matania Zvi Kochavi, Caesarea (IL)

(73) Assignee: AGT INTERNATIONAL GMBH, Zurich (CH)

( * ) Notice: Subject to any disclaimer, the term of this patent is extended or adjusted under 35 U.S.C. 154(b) by 0 days.

(21) Appl. No.: 15/133,344

(22) Filed: Apr. 20, 2016

(65) Prior Publication Data
US 2017/0005958 A1    Jan. 5, 2017

Related U.S. Application Data

(60) Provisional application No. 62/153,019, filed on Apr. 27, 2015, provisional application No. 62/251,209, (Continued)

(51) Int. Cl.
*H04W 4/04* (2009.01)
*H04L 12/58* (2006.01)
(Continued)

(52) U.S. Cl.
CPC ........ *H04L 51/046* (2013.01); *G06F 19/3418* (2013.01); *H04L 67/306* (2013.01);
(Continued)

(58) Field of Classification Search
CPC ..................................................... H04L 51/046
(Continued)

(56) References Cited

U.S. PATENT DOCUMENTS

| 5,692,215 A | 11/1997 | Kutzik et al. |
| 2012/0083237 A1 | 4/2012 | Fish et al. |

(Continued)

OTHER PUBLICATIONS http://postscapes.com/smart-outlets (Apr. 3, 2015).
(Continued)

*Primary Examiner* — Michael T Vu
(74) *Attorney, Agent, or Firm* — Browdy and Neimark, PLLC

(57) ABSTRACT

A client system for monitoring elders in a residential setting, the client system comprising communication apparatus operative for sending real time localization data and elder body motion data toward at least one server configured for performing at least one elder-supporting backend service responsive to at least one of THE real time localization data and elder body motion data; and at least one real-time location subsystem including: at least one wearable ("tag") including at least one ultra-wide-band (UWB) communication transceiver and an accelerometer operative for sensing at least one body motion of an elder wearing the tag thereby to provide the elder body motion data; and at least one anchor device for deployment in an elder's domicile including an ultra-wide-band (UWB) communication transceiver operative for real time sub-meter localization of the tag, thereby to provide the real time localization data.

30 Claims, 8 Drawing Sheets

Related U.S. Application Data filed on Nov. 5, 2015, provisional application No. 62/298,581, filed on Feb. 23, 2016.

(51) Int. Cl.

| | |
|---|---|
| *G06F 19/00* | (2011.01) |
| *H04L 29/08* | (2006.01) |
| *H04W 4/00* | (2009.01) |
| *H04W 4/02* | (2009.01) |
| *H04W 4/22* | (2009.01) |
| *H04B 1/3827* | (2015.01) |
| *H04W 84/04* | (2009.01) |

(52) U.S. Cl.
CPC ........... *H04W 4/008* (2013.01); *H04W 4/027* (2013.01); *H04W 4/043* (2013.01); *H04W 4/22* (2013.01); *H04B 1/385* (2013.01); *H04W 84/042* (2013.01)

(58) Field of Classification Search
USPC ............................................ 455/456.1–456.6
See application file for complete search history.

(56) References Cited

U.S. PATENT DOCUMENTS

| | | | |
|---|---|---|---|
| 2013/0095459 A1 | 4/2013 | Tran | |
| 2013/0122807 A1* | 5/2013 | Tenarvitz | H04B 5/0031 455/41.1 |
| 2013/0321145 A1* | 12/2013 | Ranieri | G06F 19/327 340/539.12 |
| 2015/0020571 A1 | 1/2015 | Chan et al. | |
| 2015/0074036 A1 | 3/2015 | Lenz et al. | |
| 2015/0234880 A1 | 8/2015 | Huber et al. | |
| 2015/0281653 A1 | 10/2015 | Frangiadakis et al. | |
| 2015/0324107 A1 | 11/2015 | Van Di Jkman et al. | |
| 2015/0339346 A1 | 11/2015 | Berchtold et al. | |
| 2015/0363643 A1 | 12/2015 | Huber | |
| 2015/0363706 A1 | 12/2015 | Huber et al. | |
| 2016/0012589 A1 | 1/2016 | Hamer et al. | |
| 2016/0014305 A1 | 1/2016 | Schlattmann | |
| 2016/0026898 A1 | 1/2016 | Abad et al. | |
| 2016/0026919 A1 | 1/2016 | Kaisser et al. | |
| 2016/0040375 A1 | 2/2016 | Van Kasteren | |
| 2016/0063057 A1 | 3/2016 | Ziekow | |
| 2016/0065669 A1 | 3/2016 | Van Dijkman et al. | |

OTHER PUBLICATIONS

Glascock, Anthony P., and David M. Kutzik. Essential lessons for the success of telehomecare: why it's not plug and play. vol. 30. Ios Press, 2012. pp. 91-97.
http://www.prnewswire.com/news-releases/real-time-locating-systems-rtls-rfid-bluetooth-wi-fi-uwb-gps-ir-nfer-zigbee-and-emerging-technologies-and-application-market-forecasts-to-2020-253476971.html (Apr. 1, 2014).
http://en.wikipedia.org/wiki/Kernel_density_estimation (Nov. 4, 2015).
https://en.wikipedia.org/wiki/Machine_learning (Oct. 29, 2015).
http://bespoon.com/3d-precise-location-rtls/ (Nov. 1, 2015).
http://www.blinksight.com/2013/04/blinksight-and-imec-announce-worlds-first-single-chip-indoor-gps-solution/ (Apr. 15, 2013).
http://www.decawave.com/technology/scensor-and-real-time-location-systems-rtls (Oct. 26, 2015).
http://www.rfidsolutionsonline.com/doc/rtls-time-domain-and-aeroscout-introduce-the-0001 (Feb. 5, 2008).
https://www.zebra.com/us/en/solutions/location-solutions.html (Sep. 24, 2015).
https://en.wikipedia.org/wiki/Coefficient_of_variation (Apr. 10, 2015).
https://en.wikipedia.org/wiki/Aging_in_place (Oct. 27, 2015).
http://www.awarehome.gatech.edu/drupal/?q=content/research-areas-0 (2017).
http://publish-www-ufl.wcm.osg.ufl.edu/news---archive/archive/2003/11/uf-smart-home-demonstrates-concept-of-automated-elderly-help-and-care.html (2003).
Glascock, Anthony P., and David M. Kutzik. "Behavioral telemedicine: A new approach to the continuous nonintrusive monitoring of activities of daily living." Telemedicine journal 6.1 (2000): 33-44.
http://postscapes.com/smart-outlets, "Best Smart Wifi Outlets and Plugs" (2016).

* cited by examiner

Fig. 3

| | Tablet | Caregiver Dashboard | Family App | Anchors | Wearable | Attachment Appliance |
|---|---|---|---|---|---|---|
| social services e.g. ordering food/taxi | v | | | | | |
| social services e.g. VoIP with care givers | v | v | | | | |
| social services e.g. VoIP with FM, pictures from FM (family members) | v | | v | | | |
| social services e.g. VoIP with FM or care givers, pictures from FM, ordering food/taxi | v | v | v | | | |
| voice alerting & CGO notification | | v | v | v | | |
| voice alerting & FM notification | | | v | v | | |
| voice alerting & CGO/FM notification | | v | v | v | | |
| social services e.g. VoIP with care givers & voice alerting & CGO notification | v | v | v | v | | |
| social services e.g. VoIP with FM, pictures from FM & voice alerting & FM notification | v | v | v | v | | |
| social services & voice alerting & CGO/FM notification | v | | v | v | | |
| voice alerting & location based distress & ADL anomaly detection & CGO notification | | v | v | v | v | |
| voice alerting & location based distress & ADL anomaly detection & FM notification | | v | | v | v | |
| voice alerting & location based distress & ADL anomaly detection & CGO/FM notification | v | v | v | v | v | |
| social services & voice alerting & location based distress & ADL anomaly detection & CGO | v | v | v | v | v | |
| social services & voice alerting & location based distress & ADL anomaly detection & FM features | | v | v | v | v | |
| social services & voice alerting & location based distress & ADL anomaly detection & CGO/FM | v | v | v | v | v | |
| voice alerting & location based distress & ADL anomaly detection &CGO notification &outdoor | | v | | v | v | v |
| voice alerting & location based distress & ADL anomaly detection & FM notification & outdoor | | | v | v | v | v |
| voice alerting & location based distress & ADL anomaly detection & CGO/FM notification & outdoor | | v | v | v | v | v |
| social services & voice alerting & location based distress & ADL anomaly detection & CGO &outdoor | v | v | v | v | v | v |
| social services & voice alerting & location based distress & ADL anomaly & FM & outdoor | v | | v | v | v | v |
| social services & voice alerting & location based distress & ADL anomaly & CGO/FM & outdoor | v | v | v | v | v | v |

METHOD OF MONITORING WELL-BEING OF SEMI-INDEPENDENT PERSONS AND SYSTEM THEREOF

CROSS-REFERENCES TO RELATED APPLICATIONS

The present application claims priority from U.S. provisional applications Nos. 62/153,019 entitled "Systems and methods for monitoring well-being of seniors" and filed 27 Apr. 2015; and from U.S. provisional application 62/251,209 entitled "Methods And Systems For Detecting Distress Of A Person", and filed 5 Nov. 2015; and from U.S. provisional application 62/298,581 entitled "Method of distress detection . . . " and filed 23 Feb. 2016; these applications are incorporated hereby by reference in their entirety.

TECHNICAL FIELD

The presently disclosed subject matter relates to real time location systems and, more particularly, to real time location systems for monitoring elders.

BACKGROUND

According to Wikipedia: Aging in Place is an initiative developed to help America's communities become places that are good for seniors to live in. A similar network is the Elder Villages.

Aging in Place refers to the desire of elderly people to age independently at home (rather than in a medical facility), but at the same time to feel safe, protected and cared for. There are a number of technical approaches that aim to enable such an environment at the home of the elderly person(s) based on the use of unobtrusive sensors and optionally body worn sensors embedded in Wearables (e.g., Smart Watches) and/or Smart Mobile Devices (e.g., Smart Phones). The fixed ambient sensors are installed in the home and are monitored automatically, activating an alarm or notification when needed—this approach is known as Ambient Assisted Living (AAL).

Smart homes help promote aging in place by physiological monitoring, functional monitoring for emergency detection and response, safety monitoring and assistance, security monitoring and assistance, social interaction monitoring and assistance and cognitive and sensory assistance.

Georgia Institute of Technology has developed an in-home monitoring system that can inform family members about an older relative's daily activities, health status, and potential problems. A smart house by University of Florida has created smart refrigerators and pantries which can detect food consumption.

*Behavioral Telemedicine: A New Approach to the Continuous Nonintrusive Monitoring of Activities of Daily Living* (Telemedicine Journal 6(1):33-44, May 2000) by Anthony P. Glascock and David Kutzik describes a fully automated, passively activated data-acquisition system for routine, continuous, nonobtrusive monitoring of selected activities of daily living and production of a behavioral record for trend analysis. The monitoring system uses heat, motion, vibration, and electric current sensors-to record presence or absence of selected behavior and time and frequency of sensor signals. The individual is not required to wear apparatus nor press buttons because objects in the environment are electronically monitored, not the elder.

The references cited above and herein teach technology known in the art that may be applicable to the presently disclosed subject matter. Therefore the full contents of these publications are incorporated by reference herein where appropriate, for appropriate teachings of additional or alternative details, features and/or technical background.

GENERAL DESCRIPTION

Acryonyms

BLE: Bluetooth Low Energy
FM-CW: Frequency-modulated continuous-wave
PIR: passive infrared sensor
TDOA: Time Difference of Arrival In accordance with certain aspects of the presently disclosed subject matter, there is provided a method and system for real time localization of elders.

In accordance with other aspects of the presently disclosed subject matter, the following embodiments are provided:

Certain embodiments seek to provide systems and methods to identify falls and/or other forms of elder (say) distress, e.g. based on generated knowledge regarding a senior's daily routine e.g. in terms of her or his activities of daily life—ADLs), e.g. based on accurate indoors location tracking, e.g. utilizing wearable based UWB sensing and/or thermal sensing.

Certain embodiments seek to integrate various elder-serving components into a unified synergetic system particularly suitable for "living in place" and including some (any subset of) or all of:
  a wearable panic button that the senior should press when in distress, at least indoors. This may also include some (any subset of) or all of: a CPU with volatile and non-volatile memory, graphic display that shows time and date and/or notification messages, vibration actuator or other device providing haptic feedback, buttons e.g. to signal "Panic" and/or "I'm OK", accelerometer, proximity sensors, battery, Ultra-Wide-Band and Bluetooth wireless communication transceivers.
  Care giving organization (CGO) interface, providing emergency and other services for the senior
  Daily routine monitoring sensors that track and learn serior ADLs and detect and alert for anomalies e.g. in nutrition, hygiene, mobility, sleep, social activities.
  Medication adherence including assisting senior to comply with her or his prescribed medication plan
  Appliance providing a communication channel and operative for tracking location of senior when out of home to enable wearable "Panic" button functionality when Senior is out of home
  terminal for displaying alert related notification, medication adherence information and managing supplementary services including e.g. tele-health communication with doctor/nurse, ordering taxi, meals, cleaning services, etc.
  integrated platform for voice, video and text communication with family and friends, digital pictures album displaying photos sent from family members.
  anchor/s operative for providing communication with wearable and/or for determining wearable's location and detecting audio information e.g. spoken distress phases Certain embodiments seek to use AoA (Angle of arrival) technology for location resolution to simultaneously reduce the number of anchors required per residence and achieve high e.g. sub 1 m accuracy.

Certain embodiments seek to use dynamic blinking for reducing wearable battery consumption by supporting plural rates of position ranging and alternating therebetween e.g. at least according to the senior's estimated level of movement.

Certain embodiments seek to provide a UWB system including a wearable tag for indoor localization, and wherein power consumption optimization in UWB transmission and reception (e.g. use of dynamic blinking rate whereby ranging is less frequent ranging when senior is static), and optimal anchor selection when working in TWR (two-way ranging) mode to combine angle and distance data) enables a small battery to last several weeks between re-charges. Typically, Angle-of-Arrival (AoA) anchors are employed to enable a single anchor to determine its own distance and angle relative to the wearable (aka tag) and to determine, either locally or remotely, the spatial coordinates of the wearable accordingly, without recourse to any other anchor, thus reducing total number of required anchors, hence cost and complexity.

It is appreciated that distress may at times be detected by the server, based on location and time alone. For example, if the wearable is found by the anchor to be present in the hallway for an abnormal amount of time, then irrespective of elder motions, the server may alert emergency services (unless the elder presses her or his "I'm OK" button (aka ok button) or otherwise signals to the server that this is a false alarm).

It is appreciated that distress may at times be detected by the server, based on location in combination with elder body motions. For example, the server could be configured to alert emergency services (unless the elder presses her or his "I'm OK" button or otherwise signals to the server that this is a false alarm) responsive to a combination of: a certain profile of elder body motions, and/or a certain location of the wearable and/or a certain time of the day and/or week and/or year.

According to certain embodiments, the angle of the wearable relative to the anchor's antenna array is determined, e.g. to allow the wearable to be localized at high e.g. sub-meter accuracy or at an accuracy of less than 1 meter, or even, according to certain embodiments, less than 0.5 meter, even by a small number of anchors in a furnished residence, however this is not intended to be limiting. The small number of anchors may for example be one anchor per room, one anchor per 2 or 3 rooms, one anchor per residence, less than 10 or less than 5 anchors per 2-3 room residence rather than more than 5 or more than 10, or any other reduction in the number of anchors which still, by virtue of determination of wearable-anchor angle, allows the wearable to be real-time localized at sub-meter accuracy. This level of localization accuracy is useful for distress detection because an elder's location context may be determined accurately enough to allow useful deduction at furniture or appliance e.g. the elder may be determined to be on the sofa or bed, or near the sofa or near bed, or distant from any position typical for the elder for long residence, e.g. in the middle of living room. This level of accuracy also facilitates determination of whether or not a person is immobile or suffering from reduced mobility, e.g. crawling. This level of localization accuracy is useful for ADL recognition since its provision obviates the need for installation of sensors on household fixtures and appliances e.g. refrigerator, toilet, to determine senior ADL patterns, since accurate localization may be employed to deduce senior ADL without any need for cumbersome sensors which are difficult to install and potentially a source of annoyance to the senior.

According to certain embodiments, for facilitating automatic anchor topology discovery despite obstructions (e.g. walls) between the anchors (non-line-of-sight paths) temporary anchor devices are provided which are temporarily deployed such that from a permanent anchor designated "root", 3 different paths exist to each other anchor. The paths may be multi-hop such that each path includes or transverses plural direct e.g. clear-line-of-sight spans (aka hops) between permanent or temporal anchors. The 3 different multi-hop paths each include only clear-line-of-sight spans, and the last span (along a path extending from the root anchor to a permanent or temporary anchor) of each of the 3 paths must be different for the 3 paths to be considered different. This process is used to yield sub-meter localization of permanent locations of the at least one anchor device, for storage in the at least one server.

Many variations are possible, such as but not limited to any of the following examples:

Example 1

A system or method for generating at least one alarm upon detecting that a senior has been in at least one abnormal location for an abnormal time.

Example 2

A system or method according to any of the preceding examples wherein at least one of the abnormal location and abnormal time are determined individually for individual seniors, by comparing to an individual norm of times spent in various locations for that senior, generated during a senior-specific learning/training stage which may be based on heat map generation.

Example 3

A system or method according to any of the preceding examples wherein the norm is generated by machine learning.

Example 4

A system or method according to any of the preceding examples wherein at least one said location is defined in terms of interior design meta data characterizing the senior's domicile and stored in the system e.g. furniture location meta data or meta data of functional locations e.g. adjacency to a door or window or within viewing distance of a television.

Example 5

A system or method according to any of the preceding examples wherein the alarm is a "fall" alarm" and the abnormal location is defined inter alia in terms of z-axis information which distinguishes a standing person from a sitting person.

Example 6

A system or method according to any of the preceding examples wherein the at least one alarm includes a sequence of several alarms where a more serious alarm is generated if a less serious alarm is not resolved.

Example 7

A system or method according to any of the preceding examples wherein at least one alarm is generated based on combining abnormal location-time data with other data.

Example 8

A system or method according to any of the preceding examples wherein the other data comprises data indicating whether or not a senior's limbs are moving e.g. as indicated by accelerometer data, even if the senior is remaining too long in a single location.

Example 9

A system or method according to any of the preceding examples wherein the other data comprises audio data from which distress-indicative sounds such as crying or loud sounds may be derived.

Example 10

A system or method according to any of the preceding examples wherein at least one wearable sensor is employed, for example to determine whether a worn sensor normally found at a 1-meter (say) height has suddenly been detected at floor height, suggesting a fall.

Example 11

A system or method according to any of the preceding examples wherein at least one sensor mounted on a household functional item such as a utensil or window or door is employed.

Example 12

A system or method according to any of the preceding examples wherein the at least one abnormal location for an abnormal time comprises an uncompleted passage of the senior, normal passage time having elapsed, from one location to another e.g. from one room to another via a corridor.

Example 13

A system or method according to any of the preceding examples wherein the location is determined at sub-meter accuracy.

Example 14

A system or method according to any of the preceding examples wherein at least one UWB sensor is employed.

Example 15

A system or method according to any of the preceding examples wherein at least one thermal sensor is employed.

Example 16

At least one processor configured to perform at least one of or any combination of the described operations or to execute any combination of the described modules.

The scope includes, for example, the following embodiments:

Embodiment 1

A client system for monitoring elders in a residential setting, the client system comprising:
communication apparatus operative for sending real time localization data and elder body motion data toward at least one server configured for performing at least one elder-supporting backend service responsive to at least one of said real time localization data and elder body motion data; and
at least one real-time location subsystem including:
at least one wearable ("tag") including at least one ultra-wide-band (UWB) communication transceiver and an accelerometer sensing at least one body motion of an elder wearing the tag thereby to provide said elder body motion data; and
at least one anchor device for deployment in an elder's domicile including an ultra-wide-band (UWB) communication transceiver operative for real time sub-meter localization of said tag, thereby to provide said real time localization data.

Embodiment 2

A system according to any of the preceding embodiments wherein at least one real time location subsystem monitors an elder's location in real time and the server is operative to identify at least one location anomaly accordingly and to perform said at least one service accordingly.

Embodiment 3

A system according to any of the preceding embodiments wherein at least one real time location subsystem monitors a location of at least one portion of an elder's body in real time and the server is operative to identify at least one behavior anomaly accordingly and to perform said at least one service accordingly.

Embodiment 4

A system according to any of the preceding embodiments wherein the server includes logic configured for receiving data from the at least one real time location subsystem and logically deducing at least one activity being performed by the elder's body and selecting at least one attribute of said at least one service accordingly.

Embodiment 5

A system according to any of the preceding embodiments wherein the server includes logic configured for receiving data from the at least one real time location subsystem and logically deducing at least one distress situation and wherein said at least one service includes alerting emergency service providers responsive to said distress situation.

Embodiment 6

A system according to any of the preceding embodiments wherein at least one wearable device includes an input device operative to signal the server if manipulated by the elder and wherein upon deducing at least one distress situation, the server notifies the elder of deduction of the distress situation and, if the elder manipulates the input device and the input device responsively signals the server, the server cancels the distress situation, thereby to reduce false alarms without requiring a human operator to contact the elder.

Embodiment 7

A system according to any of the preceding embodiments wherein the at least one wearable device includes a first battery-operated device ("attachable appliance") having a cellular transceiver supporting outdoor communication and real time location and a second device which does not support outdoor communication and real time location.

First device complements the second device by adding out-door communication and localization capacities which may be based on a legacy cellular network. In contrast, adding out-door communication and localization functions to the second device may inconveniently increase at least one of the second device's weight, size and power requirements, e.g. due to added components such as antennae, and/or due to increased battery size. Also, existence of two separate localization devices simplifies interoperability of the system as a whole to different standards of cellular networks, since only the first device need be replaced to provide interoperability with a new cellular standard whereas the second device may remain as-is.

Embodiment 8

A system according to any of the preceding embodiments wherein the first device is configured to be mounted on an article of outerwear such as but not limited to a shoe.

Embodiment 9

A system according to any of the preceding embodiments wherein each elder's first device includes communication functionality for communicating with the elder's second device.

According to certain embodiments, each elder's first device includes Bluetooth functionality for communicating with the elder's second device or more generally any pair of elder devices equipped with Bluetooth may communicate between them as appropriate. Bluetooth supports a "pairing" procedure in which two Bluetooth devices are "paired" to facilitate subsequent exchange of data messages therebetween. Typically, during a technician's service visit for system installation, some (any subset of) or all pairs of components of an individual elder's system having Bluetooth functionality, may be paired as appropriate.

Each elder's first and second devices (and other elements of the system herein described as having Bluetooth functionality) may more generally communicate via any suitable low-power communication solution such as but not limited to Bluetooth.

Embodiment 10

A system according to any of the preceding embodiments and also comprising an elder's terminal including a CPU, memory, at least one input device and at least one output device.

Embodiment 11

A system according to any of the preceding embodiments and also comprising a cell app configured to serve at least one significant other, such as a family member, of the elder.

Embodiment 12

A system according to any of the preceding embodiments and also comprising a web client configured to serve at least one care-giving-organization end-user and wherein the elder-supporting backend service includes determining alerts, responsive to said data, requiring attention of a care-giving organization and sending said alerts to at least one care-giving organization and also comprising logic for cancelling alerts which the care-giving organization indicates, using said web client, to have been handled, logic sorting alerts not yet cancelled by urgency, and dashboard logic for displaying said alerts not yet cancelled in descending order of urgency.

Embodiment 13

A system according to any of the preceding embodiments wherein the tag has dynamic adaptive blinking functionality in which UWB transmissions by the transceiver, used for real time localization, have time intervals therebetween of variable length, corresponding to estimates of the senior's variable levels of mobility, thereby to conserve power allowing the tag to operate for longer without recharging, relative to a tag not having the dynamic blinking mode of operation.

The estimates may be generated during a learning stage in which increases and drops in the senior's level of mobility over the day or week or year is plotted; and/or may be generated or updated in real time responsive to recent level of mobility expressed by extent of change between consecutive real time location readings generated by the anchor for the senior's tag.

In accordance with other aspects of the presently disclosed subject matter, there is provided a computer-based unit configured to operate in conjunction with the system e.g. as described herein.

Embodiment 14

A system according to any of the preceding embodiments wherein the anchor device comprises an angle-of-arrival based anchor device having plural receiving elements and supporting discernment of the wearable device's current angular orientation relative to the anchor device including computation of angles of arrival of incoming radio-frequency radiation received by the anchor device, by comparing arrival times of the incoming radiation at said receiving elements respectively.

Embodiment 15

A system according to any of the preceding embodiments wherein the communication apparatus is operative for sending said real time localization data and elder body motion data toward at least one server operative for performing at least one elder-supporting backend service selected by comparing elder body motion data to a stored profile of elder body motion data characterizing an elder location indicated by said real time localization data.

Embodiment 16

A system according to any of the preceding embodiments and also comprising temporary anchor devices which support sub-meter localization of permanent locations of said at least one anchor device, for storage in the at least one server, when the temporary anchor devices are temporarily deployed such that:

said at least one anchor device includes only anchor devices having a path to a permanent anchor designated "root", and such that at least one and preferably plural different paths exist from the root anchor to each other anchor.

The paths (3, preferably, or 1 or 2) could be multi-hop i.e. may include plural spans between pairs of permanent or temporary anchors. Typically, the plural e.g. 3 different multi-hop paths include only clear-line-of-sight spans or hops, and at least a last span (or hop) from a sequence of spans extending from the root anchor to a permanent or temporary anchor must differ between paths for paths to be considered different.

Embodiment 17

A system according to any of the preceding embodiments wherein said server and said client system are within a single residence and communicate via a LAN.

Embodiment 18

A method for monitoring elders in a residential setting, the method comprising providing a client system, including:

Providing communication apparatus operative for sending real time localization data and elder body motion data toward at least one server configured for performing at least one elder-supporting backend service responsive to at least one of said real time localization data and elder body motion data; and Providing at least one real-time location subsystem including:
  at least one wearable ("tag") including at least one ultra-wide-band (UWB) communication transceiver and an accelerometer sensing at least one body motion of an elder wearing the tag thereby to provide said elder body motion data; and
  at least one anchor device for deployment in an elder's domicile including an ultra-wide-band (UWB) communication transceiver operative for real time sub-meter localization of said tag, thereby to provide said real time localization data.

Embodiment 19

A computer program product, comprising a non-transitory tangible computer readable medium having computer readable program code embodied therein, said computer readable program code adapted to be executed to implement a method for monitoring elders, said method comprising:
  employing communication apparatus operative for sending real time localization data and elder body motion data toward at least one server configured for performing at least one elder-supporting backend service responsive to at least one of said real time localization data and elder body motion data; and
  employing at least one real-time location subsystem including:
    at least one wearable ("tag") including at least one ultra-wide-band (UWB) communication transceiver and an accelerometer sensing at least one body motion of an elder wearing the tag thereby to provide said elder body motion data; and
    at least one anchor device for deployment in an elder's domicile including an ultra-wide-band (UWB) communication transceiver operative for real time sub-meter localization of said tag, thereby to provide said real time localization data.

Embodiment 20

A method according to any of the preceding embodiments and also comprising alerting for possible distress based on sensing of senior voice data by said at least one anchor device and detection of predetermined phrases indicative of possible distress, within said senior voice data.

BRIEF DESCRIPTION OF THE DRAWINGS

In order to understand the invention and to see how it can be carried out in practice, embodiments will be described, by way of non-limiting examples, with reference to the accompanying drawings, in which:

FIG. 3 is a simplified table useful in understanding certain embodiments of the present invention.

DETAILED DESCRIPTION

Figure 1:
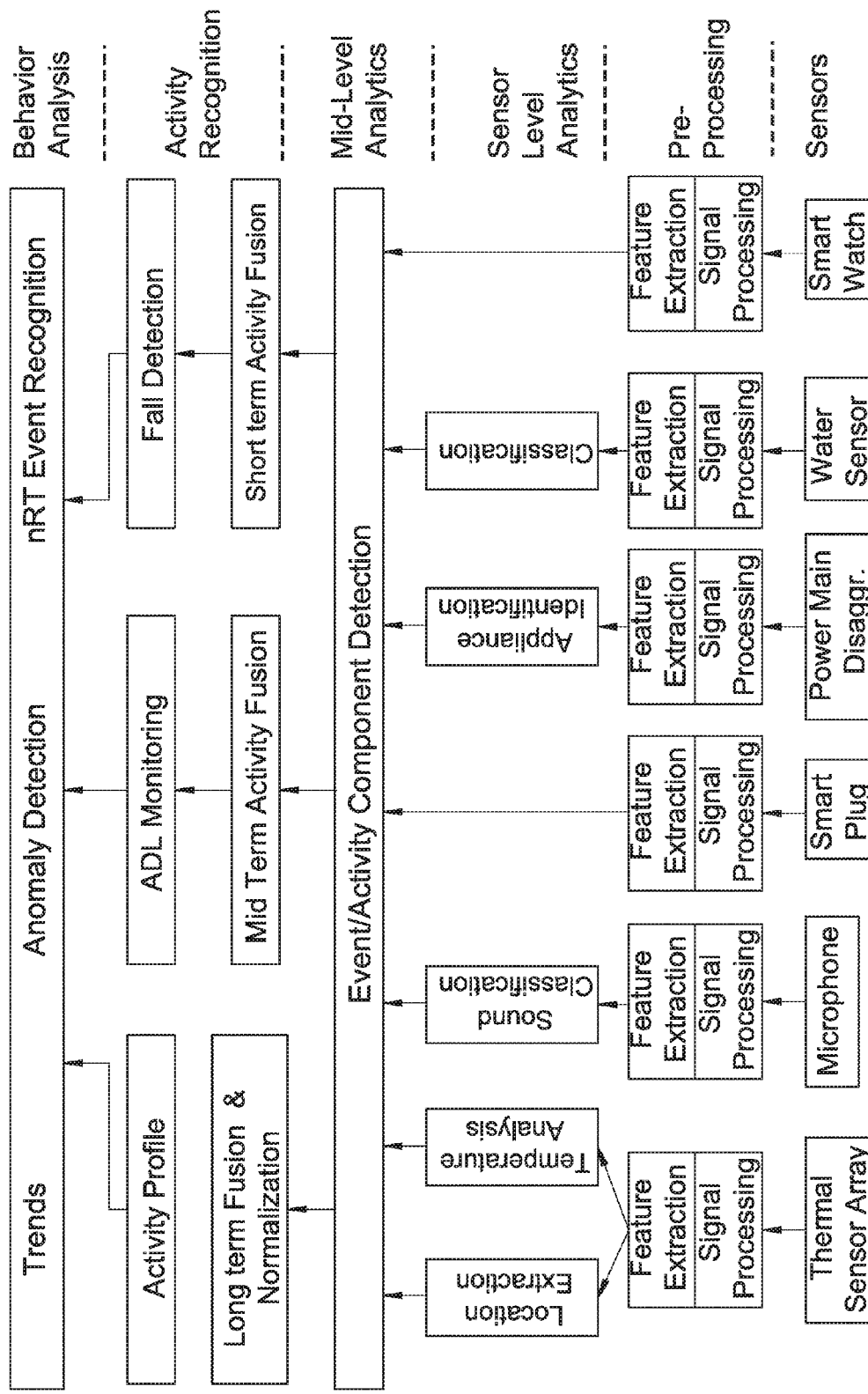
FIG. 1 is a diagram illustrating functionality, some (any subset of) or all of which may be provided, either standalone or in conjunction with apparatus and methods described herein e.g. as capabilities of the backend server of FIG. 2, all in accordance with certain embodiments of the present invention.

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter. Unless specifically stated otherwise, as apparent from the following discussions, it is appreciated that throughout the specification discussions utilizing terms such as "processing", "computing", "representing", "comparing", "generating", "assessing", "matching", "updating" or the like, refer to the action(s) and/or process(es) of a computer that manipulate and/or transform data into other data, the data represented as physical, such as electronic, quantities and/or the data representing the physical objects. The term "computer" should be expansively construed to cover any kind of electronic device with data processing capabilities. It is to be understood that the term "non-transitory memory" is used herein to exclude transitory, propagating signals, but to include, otherwise, any volatile or non-volatile computer memory technology suitable to the presently disclosed subject matter. It is also to be understood that the term "signal" used herein excludes transitory propagating signals, but includes any other signal suitable to the presently disclosed subject matter. The operations in accordance with the teachings herein may be performed by a computer specially constructed for the desired purposes or by a general-purpose computer specially configured for the desired purpose by a computer program stored in a computer readable storage medium.

The following terms used in this patent specification should be construed as follows: Tag: intended to include any physical element whose position is located and tracked by an RTLS system, typically battery operated mobile device with wireless communication transceiver that communicates with anchors for the purpose of localization and/or exchange of data messages.

Anchor: intended to include any unit that wirelessly communicates with a tag, e.g. as part of an RTLS solution, for resolving the tag position and/or exchanging data messages. Typically the anchor position is assumed to be known e.g. at predetermined accuracy, by a-priori information or by computation or by a combination of both.

Embodiments of the presently disclosed subject matter are not described with reference to any particular programming language. It will be appreciated that a variety of programming languages may be used to implement the teachings of the presently disclosed subject matter as described herein.

Bearing this in mind, attention is drawn to the following description:

Certain embodiments seek to provide an AAL solution characterized by at least one of:
  Privacy preservation—for example, for certain use cases it may be desired to use ambient sensors which do not include video cameras that allow identification or recognition of specific people and/or to refrain from use of continuous speech capture, analysis or recognition. Other use cases will not impose these constraints.
  medical diagnostics is not required—the analysis of the sensorial data will not include a medical diagnosis, it may include physiological/bio sensing
  precondition medical diagnostics may improve analytics and thresholds Our AAL solution, according to certain embodiments, may use ambient and/or body worn sensors, the sensor data analyzed to achieve some or all of the following three goals:
  Fall Detection—this is one of the most critical aspects for aging people, as the risk of falling increases sharply with age. In many fall situations immediate care is required; it is also quite common for people who have fallen and live by themselves to be unable to call for help or help themselves. Our solution detects falls with high probability, while minimizing the probability of false alarms.
  Distress detection—similar to falls, there are other events when a senior requires immediate help and unable to get it, the system detects such distress situations such as not getting up from bed/sofa/chair. Getting stuck in a room.
  ADL Monitoring—Activities of Daily Living (ADLs) are routine activities undertaken as part of daily life and include areas such as food preparation, eating, self-hygiene, sleeping, etc. Typically, ADL degradation—even a slow one over days and weeks—may indicate the need for medical intervention. Changes in ADLs may be caused by different underlying ailments, however our solution may provide the alert and leave the underlying cause determination to medical professionals.

In order to achieve these goal/s under the previously stated constraint/s, our solution may employ sensing of very specific phenomena and then the application of very specific signal processing and data analytics approaches. Specifically, we may rely on highly accurate, continuous and near real time determination of the location of the elderly person in their home. Other phenomena, such as but not limited to energy usage, may also be sensed. This may employ a Real Time Location System (RTLS) that operates in and around the home (i.e., indoors and outdoors close to the home). We consider both RTLS that uses fixed ambient sensors, as well as body worn sensors.

While accurate outdoor RTLS based on GPS receivers, installed in Smart Phones, has become quite straightforward, the same cannot be said about indoor RTLS, which may be employed by our solution. GPS cannot be relied on indoors and the accuracy provided by our solution exceeds standard GPS. We typically employ sub meter accuracy (preferably in all 3 spatial dimensions) in order to determine, for example, if the person is in front of the refrigerator or 1 meter to the left, in front of the stove. Additionally, being able to differentiate between the worn sensor being at a 1-meter height relative to the floor and at floor level enables the detection of a potential fall.

This disclosure includes an embodiment wherein RTLS, indoors and outdoors, is used as a specific and major part of an AAL solution for elderly people wishing to age independently in the comfort of their own home, while feeling safe and protected.

Example System Workflows are now described.

The solution may include two parallel workflows:
1. Analysis of Routines and/or ADLs—ADLs (Activities of Daily Living) define the daily routine of a senior. By collecting the senior's ADLs and analyzing them, the system can detect and alert on abnormal changes that may require intervention of a care giver or a family member.
  The system includes some or all of the following layers for analysis of routines and/or ADLs:
  a. Event Detection—an event can be detected by a single sensor or multiple sensors. The list of sensors is defined in the sensors chapter below.
  b. Activity Recognition—while an event is defined as a single action (opening a refrigerator, closing the oven or taking out a plate from a cabinet), an activity is defined as an aggregation of events to a continuous activity (such as food preparation or eating). The list of activities or events any or all of which may be recognized by the system may for example include potential distress situations such as: person lying on the floor without moving; person not moving for too long; person quiet for too long; a fall as detected by an accelerometer or a yell.
  c. Behavior Modeling—the senior's activities are aggregated by a behavior modeling engine that defines a normal routine. The routine can address the activity's length, hours, number of events per day, activities order, etc.

Typically, behavior analytics generates a personalized pattern for each senior; then the anomaly detection layer (e.g. as described below) identifies anomalies specific to this specific person. Common minimum and maximum thresholds across a population of seniors may be employed, for example: sitting in a bathroom for over 2 hours may be deemed a danger signal.

d. Anomaly Detection—after a routine has been created, the system will compare a new activity to the behavior model and will alert on abnormal behaviors. Anomaly detection may be employed alternatively or in addition to a rule based approach employing thresholds. Any suitable method may be employed to efficiently determine normal ranges for anomaly detection purposes. For example, thresholds for determining an anomaly may be based on external expert knowledge supplied by medical professionals and may be stored in a suitable threshold database.

2. Distress Detection—distress can address any of the following situations:

a. Fall—unconsciousness—a senior falls to the ground and lose consciousness. The senior is located for an abnormal time in an abnormal location and is not moving.

b. Fall—conscious—a senior falls on the ground but does not lose his conscious. The senior can crawl on the floor but cannot stand up or press an alarm pendant.

c. Distress—without a fall—a senior is sitting\lying on a bed\sofa\toilet\chair—and cannot get up. The senior can be conscious or unconscious.

The layers for routines and ADL analysis described above are also useful to identify distress situations. As an example: the anomaly detection is useful to identify abnormal presence in location for period of times, thus indicating a fall accompanied by loss of consciousness.

Sensors

The solution can include all of or any subset of the following components:

1. RTLS (Real Time Location System) components for ADL extraction, based on the following technologies:
  Non Wearable including all of or any subset of:
    Thermal
    Radar based technologies (FMCW or other)
    Ultra Sonic
    Non-intrusive camera—e.g. 3D analysis
  Wearable including all of or any subset of:
    UWB (Ultra Wide Band)
    Magnetic Field
    Accelerometer
    Barometer
    BLE
    RFID 2. Non RTLS sensors:
  Non Wearable including all of or any subset of:
    Audio
    Magnetic sensors (contact)
    PIR (Infra-Red)
    Camera
    Water Sensors
    Pressure sensors
    Electricity/energy sensors
  Wearable including all of or any subset of:
    Biometric sensors (Heart Rate, SpO2, Pulse, Blood Pressure, body temp, etc.)
    Accelerometer
    Barometer
    Proximity The RTLS sensors list above can be fused with non RTLS sensors such as but not limited to an RTLS wearable that provides accurate location, fused with energy/electricity sensor to indicate specific usage of a facility (e.g. oven), or a water sensor in sink and audio sensors to differentiate between washing hands and brushing teeth in order to improve detection rate. The fusion of RTLS and non RTLS sensors is useful to provide a safety layer where one of the sensors is out of order or a wearable is not worn by the person.

Any subset of or all of the following may be provided, e.g. for distress detection:

1. Training Phase—RTLS routine analysis—In order to define the senior's routine and to be able to detect an abnormal behavior, a training phase will take place after the system is installed. During the training phase the system will create a heat map or other representation of the senior's movement in the house, and will be able to indicate the expected time the senior stays in each location such as specific rooms or such as within proximity to specific "landmarks" in the senior's environment such as her or his microwave oven, refrigerator, bed, chairs or toilet. The behavioral model will be personalized to the senior's routine and house structure.

2. Anomaly location analysis—the system will raise an alert if a senior stays an abnormal time in a location. The expected time can vary based on the location (i.e.—the expected time on the sofa can be up to 2 hours, while an expected time on the floor can be up to 1 minute).

It is appreciated that any suitable method may be employed to generate location data e.g. the location of Senior1's refrigerator, Senior2's armchair and Senior3's corridor. For example, the layout of the home may be captured during setup and installation in a suitable object location database and may include measurements of the rooms' dimensions and/or location of furniture and appliances.

3. Crawling—the system can also indicate an abnormal pattern of movement that represents crawling. For example, the system may detect a person who is moving, but whose Z-axis location indicates that she or he is not standing up. And/or; the system may detect a person who cannot stand up, but still moves in an abnormal pattern on the floor.

4. Fusion with Z Axis sensors (UWB\Barometer)—if Z axis location information can be provided (e.g. by using a Barometer, FMCW Radar, UWB based on 4 anchor-TDOA) the system can distinguish a senior that is lying on the ground from a senior that is standing or sitting.

5. Fusion with an accelerometer—accelerometer can be used in two main scenarios:

a. Accelerometer as a trigger for fall detection: An accelerometer can detect a fall by detecting movement in a high acceleration.

b. Accelerometer as a complementary indication to an RTLS event: the accelerometer can also be used after an abnormal behavior is detected by an RTLS sensor. The accelerometer can detect if the senior is moving or not and improve the alert certainty.

6. Night fall and shower fall—The solution typically includes additional mechanisms for detecting distress in cases a wearable device is not being worn:
   a. Proximity sensor—the wearable device includes a proximity sensor that can indicate if the device is being worn or not. The event of taking off the device is being monitored by the system and is addressed as part of the routine. In case the system identifies the event as part of a shower activity and the device is not worn back in a reasonable timeframe the system can raise an alert.
   b. Voice activation—the solution typically includes microphones that can be located in the house surroundings or on the wearable device. The system can identify if a person is calling for help, crying or moaning—and use the information to raise an alert.
   c. Abnormal time between sensors—an alert can also be raised if a person disappears between areas in an abnormal pattern. (For example—person moving between two rooms and falls in the corridor. The system can detect a fall based on the fact the person did not reach the second room in an abnormal time)
7. Workflow management—using user feedback to improve true positive: false alarm ratio—the solution typically includes a workflow engine that can decide if and when to send an alert to each stakeholder (the senior, a family member, care giver, etc.). The workflow engine can send the alert to the senior before escalating the alert to additional users. In case of a false alert—the senior can cancel the alert from the wearable device. If the senior does not respond to the alert in a predefined timeframe the alert will be sent to additional stakeholders.
   a. Update system configuration based on user feedback—user feedback can be used to fine tune system configuration. For example—the system can indicate a person is located an abnormal time on the floor—Z-axis information indicating a person is lying on the floor may even trigger an alert regardless of time spent; and send an alert to his wearable device. The user can cancel the alert (as he has moved a chair to that location). The system will use this information and change the alert threshold of this location.
8. Meta Data—the system can use externally provided contextual metadata characterizing individual seniors, to personalize alert thresholds for that senior. For example—a senior known to suffer from with Alzheimer disease in stage 4 will raise an alert when leaving the house in the evening whereas those not suffering from same will not raise an alert when leaving the house in the evening; a senior confined to a wheelchair can raise an alert if he or she is sitting for long periods in areas that were defined as floor (e.g. were defined as portions of the senior's domicile which do not include any particular functional value as opposed to portions of the house which do have known functional value hence behavior patterns such as the senior's bed or chair or toilet or in front of the senior's stove or fridge) whereas those not confined to a wheelchair might only raise an alert if their Z-axis information indicates they are lying on the floor but not if they are standing, etc.

Any suitable combination of the data collected as described herein may be used to generate suitable alert rules. For example, a default "senior is not eating" rule might be: alert senior if 0 (zero) fridge opening episodes are detected in at least one 6 hour period between 8 am and 8 pm, and alert organization/relative if 0 (zero) fridge opening episodes are detected between 8 am and 8 pm, where "fridge opening episode" is defined as: senior remains within less than 0.5 meters of the known fridge location for at least 30 sec.

However, the default rule might be personalized e.g. if a heat map, upon analysis, yields specific eating routines followed by an individual senior.

Any suitable technology/ies may be employed separately or in combination to detect human presence and to determine adjacency to known functional locations such as a known fridge location; such as but not limited to Acoustic sensors; Image recognition of human shapes; Infrared detectors; Pressure-sensitive floor tiles; Radar; Chemical sensors; and/or Detection of mobile phone, Bluetooth, or Wi-Fi signals of a device borne by the senior.

1. The solution can include several wearable devices from different types (wristband, necklace, shoe\ slippers, etc.)—the system can detect that a sensor is being worn utilizing a proximity sensor or bio sensing (such as heart rate) and address this sensor as the real location of the person. The system awareness of whether or not a wearable sensor is being worn may be used also for reminding the senior to wear the sensor.
2. Calendar—the system can also address calendar events as additional input:
   a. Medications calendar events—when fused with location or other sensors—the system can decide to alert a medication was not taken on time:
      i. The medication plan may be inserted in advance into the system by the senior or family via suitable interfaces.
      ii. When it is time for taking medication the system notifies the senior, and/or a designated other person (e.g. family member) through interfaces (e.g. a wearable vibrating device, a notification over TV, an automated phone call, a mobile app alert, SMS, web/tablet app alert)
      iii. The senior may provide feedback that the medication has been taken
      iv. The system can receive notification from a pillbox through its sensors or from an sensor on the pillbox that the pillbox has been manipulated, thus extracting that pills are taken
   b. Leaving the house, visitors in the house—by having an outdoor activity in the calendar (for example—a doctor visit)—the system can alert if the RTLS sensor indicates the senior is in the house when the outdoor activity is scheduled.
   c. The system can also alert when a visitor should have come and didn't based on the RTLS sensors (for example—cleaner, technician, etc.) e.g. using a subset of the sensors mentioned above such as contact sensor on a door, PIR, audio sensors the system can detect the presence of additional people, and cross it with the scheduled visit.
   d. The system may also include an RFID component and RFID reader to identify service provider coming to register their specific presence
3. The system can also use movement patterns in order to distinguish between 2 seniors in the same house, or to distinguish a pet from the senior. Movement patterns may include typical speed and acceleration, and walking sounds.

Example Application Design for a care giver or care contact center may include a displayed list of alerts now pending, in descending level of urgency. Each alert includes a specification of the senior involved and a description of the event. For example, the top event may be that Sarah Levi fell in the bathroom. A less urgent event, lower on the list, may be that Jim Jones is eating less frequently lately.

More generally, the CGO dashboard is an application for care givers and care-giving organizations that is tailored for home care. Typically:

The application includes an alerts queue—ordered by severity scoring. The dashboard enables care givers to prioritize critical events (such as falls), and to distinguish them from low priority events (such as social or nutrition decline).

The dashboard also may include some or all of the following components:

A GIS map—the map presents home addresses of seniors and family members

Video call+Chat app—for contacting the senior, family members and care givers

Wellness Reports—in depth analysis of the senior's parameters, e.g. including some or all of: movement, biometrics, sleep quality, nutrition, social activity, hygiene, etc.

Extraction of Activities of Daily Living (ADLs—high level activities such as but not limited to Bathing, Washing, Dressing, Food Preparation) may comprise inferring these activities from low-level sensor events generated by appropriately monitoring an individual such as a senior—such as "increase in energy consumption in refrigerator" (implying refrigerator was opened, which together with additional sensor indications, e.g., person in front of refrigerator, leads to "food preparation started"). The flow indicated in the attached diagram may include:

Sensor activation creating a sensor event

An aggregation of a number of sensor events over some time period into

A single activity (an ADL) and/or

An indication of a distress situation—requiring/triggering action fusing a sequence of activities into a behavior pattern Detection of changes in behavior pattern—short term (a few days or a week, e.g., eating activities significantly reduced), longer term trends (weeks and months, e.g., walking slower)—requiring/triggering action Each of the above operations may employ information processing and data analytics (which may be rule based and/or machine learning based). The former is based on the construction of logical (usually Boolean) statements such as IF x happens AND also y happens WITHIN time t, THEN do z. The latter refers to much more complex situations, for example, in Supervised Learning examples of instances and their known outcome are presented to the system (also known as the Training Phase), followed by the system creating an appropriate corresponding model, such that when presented with a new instance (with unknown outcome) the system can infer/calculate/predict the outcome.

Rule based approaches typically employ a Rule Based Engine (RBE) or Complex Event Processing (CEP, applying rules to real time streaming data). Machine learning approaches include a large variety of algorithms that address many classes of problems. In the present disclosure, activity recognition, for example, can be implemented with Hidden Markov Models (HMM), Conditional Random Fields (CRF), or others. Similarly, other parts of the system are implemented with additional algorithms. In this disclosure, both rule based and machine learning approaches can be used.

The following are some specific examples; any subset of the aspects described may be provided:

1. Fall Detection [Rule based]

Sensors used—UWB and/or thermal for location tracking; accelerometer for motion determination; microphone for distress sounds Scenario description—UWB/thermal sensors started tracking person moving from bedroom; movement stopped completely in hallway; within 10 seconds of stopped movement, the body worn accelerometer registered a sudden change in vertical speed lasting 2 seconds followed by stopped motion; within another 10 seconds the hallway microphone picked up distress related sounds (e.g., groans, yells); this state continued without change for more than 10 minutes.

Corresponding rule

IF location sensor shows abrupt stopped track

AND body worn accelerometer registers within 5 seconds a vertical acceleration exceeding 5 m/s$^2$ AND the local microphone registers within 5 seconds a sound classified (by an audio analytics module) as one of the distress sounds AND there is no further change in this state for at least 10 minutes THEN trigger a Fall Detection condition with severity=HIGH 2. Food Preparation and Eating (Health Condition related) [Machine Learning based]

Sensors used may include UWB and/or thermal for location determination; Smart Plug for appliance energy consumption monitoring; kitchen/dining room sound monitoring (e.g., clinking utensils, running water); vibration sensor on water tap for water usage monitoring; body worn accelerometer for hand motion during eating.

Smart plugs may for example comprise that described in: http://postscapes.com/smart-outlets or any other device e.g. electrical outlet which appliances plug into which is operative to measure an appliance's power consumption and transmit the readings e.g. periodically. These may be used to deduce an elder's behavior; for example, a sudden increase in energy consumption from a refrigerator's smart plug might be used as an indicator that an elder has opened her or his refrigerator.

Scenario description—initial model (built during the training phase) showed that the food preparation followed by eating includes:

Being in the kitchen (location sensors) for a variable (e.g. per senior) amount of time e.g. a couple of minutes or much more Accompanied by changes in the energy consumption (Smart Plug sensors) of the refrigerator and/or hot plate a few times during variable durations on the order of minutes Accompanied by water usage, indicated by both running water sounds (microphone) and/or the vibration sensor on the water tap a few times, during variable durations on the order of minutes Followed by moving to the table area (location sensors) and a vertical change (UWB) indicating sitting near the table and staying there for some time (minutes to an hour)

Followed by clinking sounds (microphone) from the utensils and plates indicating eating Accompanied by hand motion (body worn accelerometer) indicating eating Followed by getting up (change in vertical position indicated by UWB)

Sometimes followed by moving back to the kitchen (location sensors)

Followed by water usage indicated by both running water sounds (microphone) and/or the vibration sensor on the water tap a few times during variable durations on the order of minutes (indicating cleaning of dishes)

The model typically has flexibility in terms of time durations, sequence of sensor events, some events happening sometimes, etc. Therefore the activities of food preparation and eating will be recognized as routine even in the face of a typically predetermined extent of variability.

Behavior recognition—The initial model also indicates that these activities occur mostly 3 times a day, but sometimes could be 4 or 5 times (accounting for snacks or preparing tea)

Examples of detection of a Short term trend—over the last week or so the system may detect a slow change in the number and length of food preparation and eating (inferred from the number of the recognized activities, in turn, discovered by the corresponding sensor events), all as compared to the model of the person's routine. DAY 1 (relative to start of discovered change)—3 food prep episodes/activities but only 2 near table and additional one very short duration; DAY 2-3 food preparation episodes/activities all 3 near table but one with no utensil sounds and no motion from body worn accelerometer (no hand movement); DAY 3—only 2 food preparation activities; etc.

Figure 2:
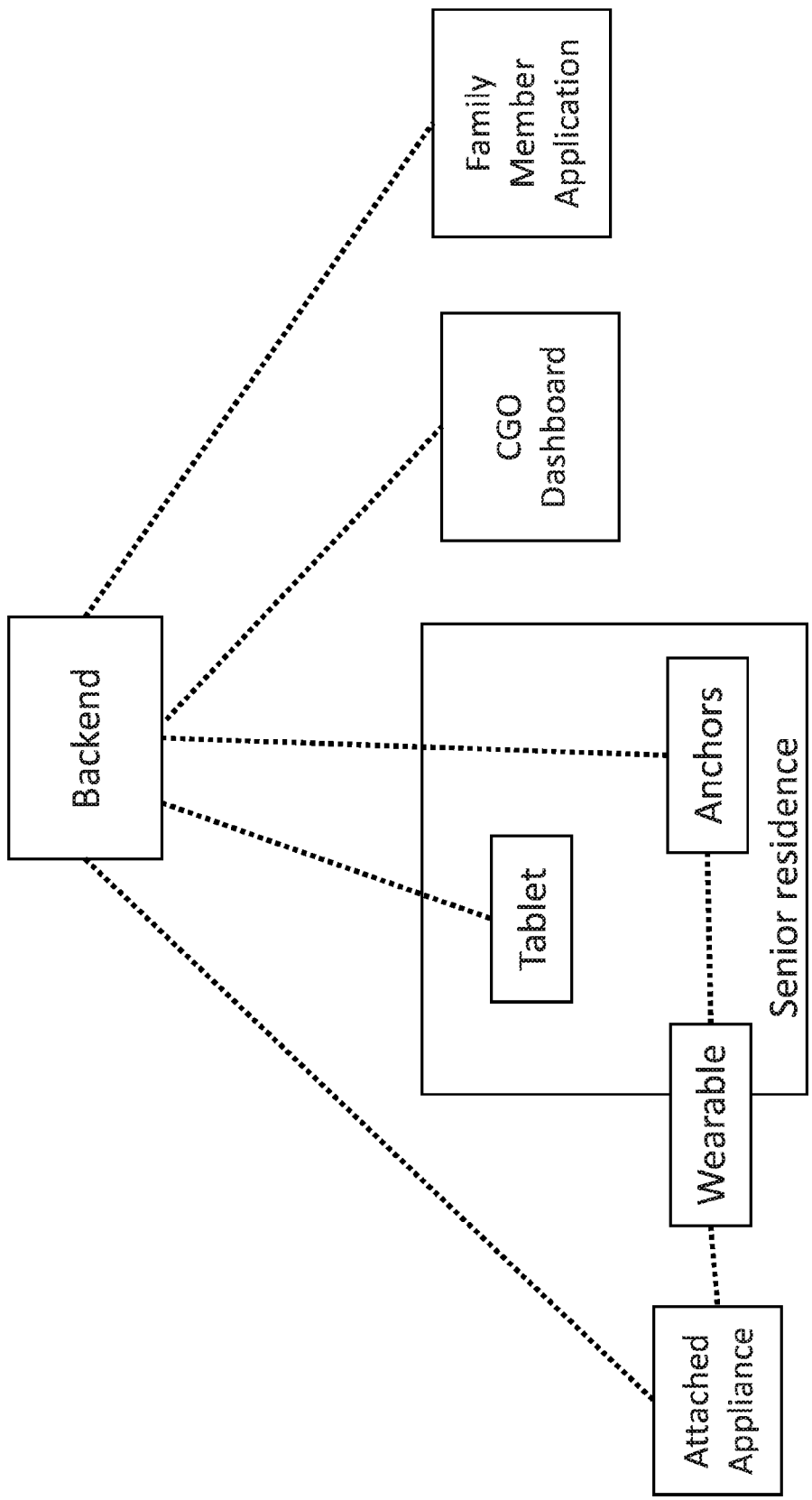
FIG. 2 illustrates a functional block diagram of a computerized client system for monitoring elders in a residential setting, and associated backend server, the client system comprising communication apparatus operative for sending the real time localization data and elder body motion data toward at least one server configured for performing at least one elder-supporting backend service responsive to at least one of the real time localization data and the elder body motion data; at least one wearable ("tag") including at least one ultra-wide-band (UWB) communication transceiver and an accelerometer sensing at least one body motion of an elder wearing the tag thereby to provide the elder body motion data; and at least one anchor device for deployment in an elder's domicile including an ultra-wide-band (UWB) communication transceiver operative for real time sub-meter localization of the wearable, all in accordance with certain embodiments of the presently disclosed subject matter.

FIG. 2 is a simplified functional block diagram of an elder monitoring system in accordance with certain embodiments; a processor can be configured with any one, some or all of functional modules described herein in accordance with computer-readable instructions implemented on a non-transitory computer usable medium. The teachings of the presently disclosed subject matter are not limited to the system described with reference to FIG. 2. Equivalent and/or modified functionality can be consolidated or divided in another manner and can be implemented in any appropriate combination of software, firmware and hardware and executed on a suitable device. The system shown and illustrated herein can be a standalone network entity, or integrated, fully or partly, with other network entities. Those skilled in the art will also readily appreciate that the data repositories can be consolidated or divided in other manner; databases can be shared with other systems or be provided by other systems, including third party equipment.

According to certain embodiments at least one real time location subsystem which may include anchor/s, wearable e.g. tag and/or attachable appliance, monitors an elder's location in real time e.g. using the anchor/s to localize the target or "wearable" worn by the senior and the server, is operative to identify at least one location anomaly accordingly and to perform the at least one service accordingly. According to certain embodiments the at least one wearable device includes a first battery-operated device ("attachable appliance") having a cellular transceiver supporting outdoor real time communication and localization and a second device which does not support outdoor communication and real time location. According to certain embodiments the first device is configured to be mounted on body wear such as but not limited to footwear such as but not limited to a shoe. According to certain embodiments each elder's first device includes communication functionality for communicating with the elder's second device.

Anchors may be configured to plug into standard wall outlet sockets, to ease deployment in a senior's household and may include some (any subset of) or all of: a Pass-through power socket, a CPU (volatile and non-volatile), microphone/s, Ultra-Wide-Band wireless communication transceiver and Ethernet port (to support connection of at least one anchor to an Internet gateway to provide communication to a backend server), and, e.g. in the case of an AoA base anchor, also an accelerometer to determine the orientation of an anchor installation e.g. with respect to the earth ground plane.

The Backend server which may of course include plural servers in data center/s or virtualized server/s and/or a cloud service typically is configured to perform some (any subset of) or all of the following functions e.g. in software: communication center with all system components e.g. some (any subset of) or all of wearable, anchors, elder terminal e.g. tablet, CGO dashboard and FM App, data portal for reception and storage of events and sensors measurements from wearables, anchors and elder terminal, distress detection including ADL anomaly detection, system integrity detection e.g. monitoring proper equipment operational functionality, automation of workflow of alerts and incidents, and management of, including initiation of, supporting senior services (such as but not limited to medication reminder, VoIP, calendar presentation). The back-end server may have any or all of the functionalities shown and described herein and/or any or all of the functionalities shown in FIG. 1. The back-end server may also store or have access to suitable data tables e.g. a table indicating which care giving organization end-user is responsible for which elder end-users, a table indicating which devices belong to each senior, a table indicating which family member app users are bound to each senior, and so forth.

The backend server may include any suitable analytics platform for contextualizing data and turning information into actionable knowledge e.g. as per any of the teachings of any of the following systems all known in the art; for each of which the published US Patent application number, date and subject matter are indicated; the disclosures thereof are hereby incorporated by reference:

| 1 | 20160063057 | Mar. 3, 2016 | Maintaining background knowledge in complex event processing |
|---|---|---|---|
| 2 | 20160065669 | Mar. 3, 2016 | Location-oriented team intercommunication |
| 3 | 20160040375 | Feb. 11, 2016 | Collapsible smart fence |
| 4 | 20160026898 | Jan. 28, 2016 | Object detection |
| 5 | 20160026919 | Jan. 28, 2016 | System and social event detection |
| 6 | 20160012589 | Jan. 14, 2016 | Automatic spatial calibration of camera network |
| 7 | 20160014305 | Jan. 14, 2016 | Automatic time signature-based video matching |
| 8 | 20150363643 | Dec. 17, 2015 | Fusion-based object-recognition |
| 9 | 20150363706 | Dec. 17, 2015 | Fusion of data from heterogeneous sources |
| 11 | 20150339346 | Nov. 26, 2015 | Registering sensors used in monitoring-systems |
| 12 | 20150324107 | Nov. 12, 2015 | Display of visual information |
| 13 | 20150281653 | Oct. 1, 2015 | Selecting sensors in surveillance applications |
| 14 | 20150234880 | Aug. 20, 2015 | Updating data structure with sensor data |
| 15 | 20150074036 | Mar. 12, 2015 | Knowledge management |

The backend service typically comprises an automated workflow engine configured to manage most incidents without having to involve a human operator, thus reducing solution cost. For example, when suspected distress is detected, the workflow engine may send appropriate inquiry messages to the senior wearable and/or terminal; when a senior fails to confirm her or his medication adherence, the workflow sends suitable reminders to the senior wearable and/or terminal, and so forth.

According to certain embodiments the backend server includes logic configured for receiving data from at least one real time location subsystem e.g. any localization component of any of the subsystems in FIG. 2, and logically deducing at least one activity being performed by the elder's body and selecting the at least one attribute of the at least one service accordingly.

According to certain embodiments the backend server includes logic configured for receiving data from the at least one real time location subsystem and logically deducing at least one distress situation and wherein the at least one service includes alerting emergency service providers responsive to the distress situation.

According to certain embodiments an elder's terminal (e.g. tablet), including a CPU, memory, at least one input device and at least one output device, is provided.

According to certain embodiments a cell app (aka "family member application" or "FM application" configured to serve at least one significant other, such as a family member, of the elder, is provided, to enable family members (e.g.) to receive distress notifications, provide picture uploads, etc.

According to certain embodiments a web client or dashboard configured to serve at least one care-giving-organization end-user is provided. The caregiver-organization dashboard need not comprise a web client, and may be implemented, say, as a native Windows/MAC-OS/Linux application. Typically, service/s provided by the elder-supporting backend server includes determining alerts, responsive to the data, requiring attention of a care-giving organization and sending the alerts to at least one care-giving organization and also comprising logic for cancelling alerts which the care-giving organization indicates, using the web client, to have been handled, logic sorting alerts not yet cancelled by urgency, and dashboard logic for displaying the alerts not yet cancelled in descending order of urgency.

The communication apparatus is typically operative for sending the real time localization data and elder body motion data toward at least one backend server which typically utilizes same for performing at least one elder-supporting backend service selected by comparing received elder body motion data to a stored profile of elder body motion data characterizing an elder location indicated by received real time localization data.

It is appreciated that any suitable communication technology may be employed herein. For example, indoor data from the wearable may be sent to anchors over UWB or Bluetooth, anchors can communicate between themselves over UWB or Bluetooth, designated anchor(s) may aggregate communication to the backend using standard IP transport services, such as but not limited to TCP and UDP. While the senior (aka elder) is outdoors the wearable may communicate with the attached appliance over Bluetooth which routes the communication to/from backend using standard IP transport services.

Typically, the backend server is able to resolve tag location and provide service/s accordingly including emergency services. Typically, each senior's tag communicates with the seniors anchors and triangulation, tri-lateration, multi-lateration or any other suitable localization technique is employed either at the server or at the residence, to localize the senior. Tracking the wearable location and/or typically pre-configured accelerometer patterns trigger a potential distress condition in the server. Typically, this condition or state can be cleared or dismissed e.g. by the relevant senior uttering a predetermined alert dismissing phrase or pressing an ok button (or activating any other typically wearable dismissing input option). Typically, a distress condition may also be triggered by the senior uttering an alerting phrase. The senior voice may be captured by microphone(s) in the anchors and analysed e.g. to detect predetermined alerting phrases.

Inter alia, the Backend service, among other services, typically sends reminders to family members to upload pictures e.g. n days after their last picture upload or m days before special calendar occasions (senior's birthday, Thanksgiving). Reminders are optionally sent at a suitable time e.g. 19:00 at the local time of the family member whose time-zone is known to the back-end service, e.g. so notification sound does not disturb sleep. Pictures or messages from family members may be immediately downloaded to the elder terminal for viewing, or may be downloaded at pre-programmed points within the seniors' learned daily schedule. If pictures have not yet been seen by the senior (elder), the backend sends a notification to the senior that new pictures have arrived, optionally at a suitable time of day e.g. if a batch of pictures arrives to the senior's terminal after 20:00 senior's local time, notification may be postponed to 08:00 the following day.

The terminal of FIG. 2 may comprise a conventional tablet or interactive console E.g. TV monitor with hand/finger orientation/gesture/touch sensor/s such as, for example, Kinect-for-xbox or any other commercially available orientation/gesture/touch sensor.

The terminal is typically fixed, e.g. in the course of a technician's service visit, to a stand configured to be placed on a desk since it is advisable to prevent or discourage the senior from detaching her or his terminal from the desk to reduce the likelihood of the terminal being lost. Alternatively or in addition, terminal loss can be handled e.g. by localizing terminal with coarse accuracy in the household based on WiFi transmission from the terminal.

The terminal may include some or all of a CPU, volatile memory, non-volatile memory, display with touch sensors, microphone, speaker, and Wifi transceiver and may be configured to provide some (any subset of) or all of the following functionality:

Displaying notifications from backend e.g. "Are you OK?" for dismissing suspected distress conditions using the tag's OK button Display medications consumption plan arriving from backend server Display medication reminders Events calendar management, and reminders, responsive to control arriving from backend server VoIP (video or only voice) calls with care givers and family members Instant messaging with care givers and family members Digital picture album showing pictures sent from family members. Typically, the backend service of FIG. 2 periodically sends notifications to the family member application end users to remind them to send pictures to the senior/s they are associated with (aka "bound" to). The family member app end user can upload pictures from his or her smart phone via the family member application to the backend server. The backend server of FIG. 2 automatically downloads the pictures to the senior terminal which may notify the senior that new pictures have arrived from family members or automatically displays the pictures sent from the family members as a digital album.

Sending at least one "binding" invitation to family members, to create an association in the backend server between an individual senior and an individual end user of the family member app of FIG. 2. Any suitable security procedure may be employed to ensure that only the senior's genuine and desired family members are bound to each senior. An example binding protocol is described below; any or all of the elements thereof, indicated by bullets, may be provided, in any suitable order; in any event the binding protocol below is intended to be merely exemplary.

The following is an example "binding" protocol for creation of an association in the backend server between an individual senior and an individual end user of the family member app of FIG. 2:

Aspects of binding protocol pertaining to the terminal of FIG. 2 may include some (any subset of) or all of:
  UI in the terminal for family member by specifying the FM phone number
  The terminal retrieves from backend the allowed phone numbers format
  The terminal presents Country code from pull down menu, area code from pull down menu and then remaining digits. Press on "Invite" sends message to backend (with phone number). Press on "Cancel" goes back
  Terminal receives notification "Binding request from FM" showing the FM name picture and relation, with options of "Accept" or "Decline".
  Press on "Accept" or "Decline" button for "Binding request from FM" notification sends accept or decline message to backend Aspects of the binding protocol pertaining to family member App of FIG. 2 may include some (any subset of) or all of:
  Family memberapp end user may specify senior for binding by specifying senior ID (e.g. social security number), or senior phone number or senior email address
  FM App may retrieve from backend allowed phone numbers format
  First user selects seniordetail method—email OR phone number OR ID. If email or ID, then user is allowed to enter text. If phone number then country code from pull down menu, area code from pull down menu and then remaining digits. Press on "Send" sends message to backend (with senior details). Press on "Cancel" goes back. Backend responds with "pending" or "accepted" if senior details match or with "unknown" if not matched. App shows status Pending if "match", otherwise error message and after press on "OK" button clears all senior details.

Aspects of the binding protocol pertaining to Backend server of FIG. 2 may include some (any subset of) or all of:
  Upon receiving request for allowed phone numbers format (from terminal or FM app)—backend may send allowed phone numbers format information
  Upon receiving "Invite FM" message from terminal, backend may send SMS to specified phone-num. Invite message text is according to the care giver organization's ID, with adding senior name and ID.
  Upon receiving request for "Senior binding" list from FM App, backend may send all existing Senior/FM state entries in the database with their state (pending or accepted)
  Upon receiving request for "add Senior binding" from FM App, backend may check Senior details. If no match, then backend may send "unknown". If match, then backend may check if Senior/FM binding state already exists. If not existing, then backend may create as "pending" and in any event may respond with state ("pending" or "accepted")
  Upon receiving "accept" message from terminal for "Binding request from FM" notification, backend may add family member to Senior CCG and update Senior/FM binding state to "accepted" and send contact list update message to terminal and FM App
  Upon receiving "decline" message from terminal for "Binding request from FM" notification, backend may delete Senior/FM (family member) binding state entry A suitable family member invite message information may be defined. A suitable allowed phone numbers format JSON may be defined e.g.

```
{"phoneFormat": [
    {"countryCode": "972", "areas": [
        {"areaCode": "02", "numDigits": 7},etc.
```

Figure 8:
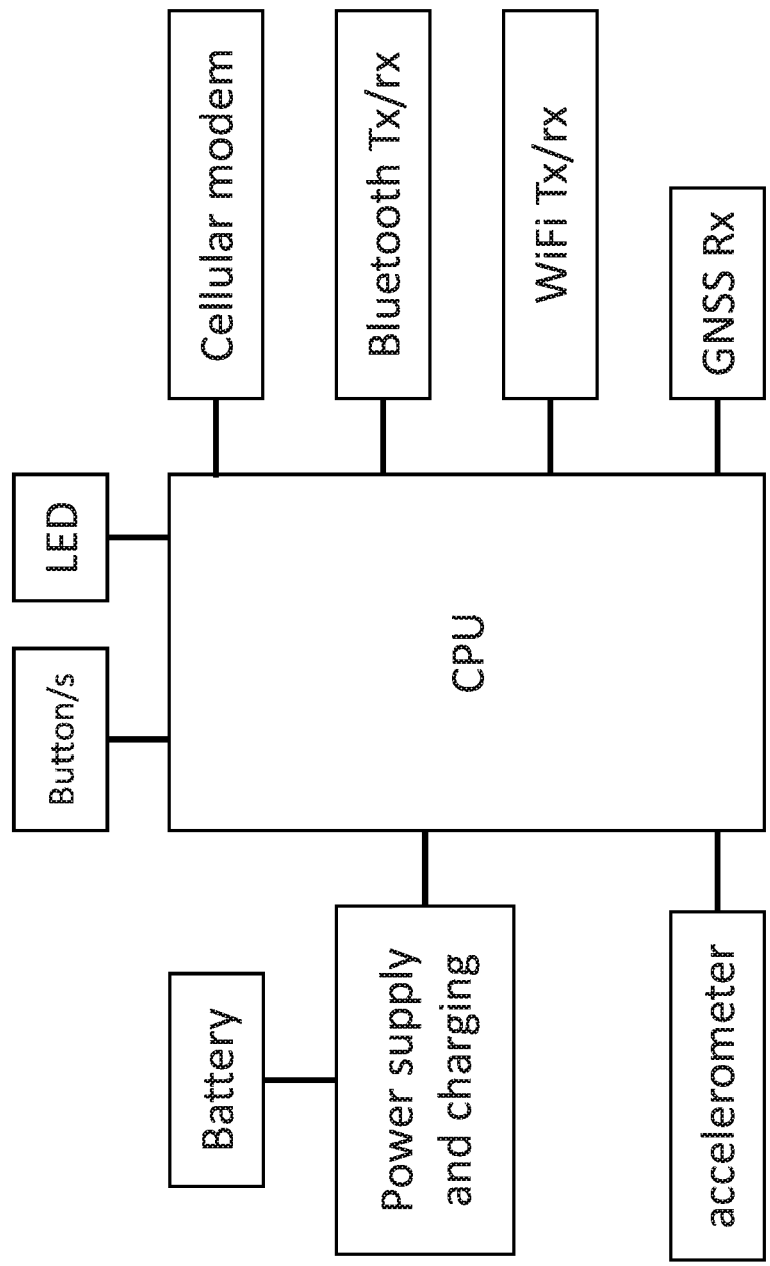

Referring again to FIG. 2, according to certain embodiments, 2 from among, or all 3 of, 3 separate client-end devices may be provided to interact with the end user: a stationary computer e.g. "tablet", a (wristwatch, or pendant e.g.) wearable or "tag" for indoor-only real time localization, and an "attached appliance" (e.g. as illustrated in FIG. 8) which may be mounted on a shoe or other article of outerwear which is ideally unlikely to be forgotten and/or infrequently laundered and/or infrequently replaced, such as a jacket or other article of outerware/clothing, shoe or other footwear, cane or walker). The "attached appliance" or alternatively an application on the senior's mobile phone provides outdoor real time localization and may employ cellular localization rather than using the anchors deployed inside the residence. Typically, at least some input device functionality e.g. the "ok" functionality on 2 or all 3 of the devices, is redundant. In this connection it is appreciated that the apparatus of FIG. 8 is not intended to be limiting and may for example be replaced by any device, whether or not attachable to senior outerware e.g. shoes that use cellular infrastructure and/or communicate with the wearable. Or, the subsystem of FIG. 8 may be omitted altogether or may be replaced by a senior outdoor cell/mobile application installed in the senior smartphone. The Wearable of FIG. 2 typically communicates with the attached appliance or senior's cell application to receive messages when out-of-home and to determine location.

Typically, the backend service of FIG. 2 is aware of which client-end equipment, e.g. the above 3 devices, are being used by the same senior. Therefore, if a dismiss for "Are You OK?" notification is activated e.g. at the terminal, the corresponding notification is responsively removed from the wearable. Similarly, if a senior confirms via one of his wearables that he has acted upon a reminder for taking medication, this clears the relevant notification from the terminal and the other wearable. The backend typically is configured not to send urgent notifications to the terminal when the backend server knows from the anchors and wearable that the senior is not at home. When the senior presses on "Panic" button on the wearable, the CGO user can make a VoIP call to the senior residence via the terminal speakers and microphone and anchor microphones.

Typically, each time a senior loses his wearable, the system aids to locate the wearable at least in the household at least for as long as the wearable battery is not drained. Typically, the wearable periodically reports the battery status to the backend. When the battery charge level drops below a certain level, the backend service automatically sends reminders to charge the wearable to the senior, and eventually, if needed, a human CGO user calls the senior to explain to senior how to effect wearable charging. The senior may be given two wearables (tags), and at any given time one is worn and the other is kept on the charger. Once the battery of the worn wearable descends to a certain level, the senior switches (e.g. is prompted to switch) the wearables e.g. to charge the tag s/he is wearing and to don the tag that is in the charger.

If the wearable can pair with a Bluetooth device that has location capabilities, the wearable can be located even if lost out-of-home. For example, a paired Bluetooth device (e.g. smartphone or attached appliance) may be configured to determine senior outdoor location e.g. using some (any subset of) or all of: cell tower signals, nearby WiFi networks, GNSS (Global Navigation Satellite System) e.g. GPS.

It is appreciated that any suitable sub-combination of the following elements: Wearable, Anchors, terminal, Care giving organization (CGO) Dashboard, Family members (FM) application, Senior outdoor application/attachment appliance (e.g. to shoe), Backend service, e.g. as illustrated in FIG. 2 may be provided such as but not limited to the sub-combinations shown in each of the lines of the table of FIG. 3. For example, anchors and/or wearables may be omitted e.g. for use cases which do not require a location based distress feature. And/or, the "terminal" may be omitted entirely or may be replaced by any elder's appliance including some (any subset of) or all of: volatile memory, non-volatile memory, display with touch sensors, microphone, speaker, and Wifi transceiver.

Figure 4:
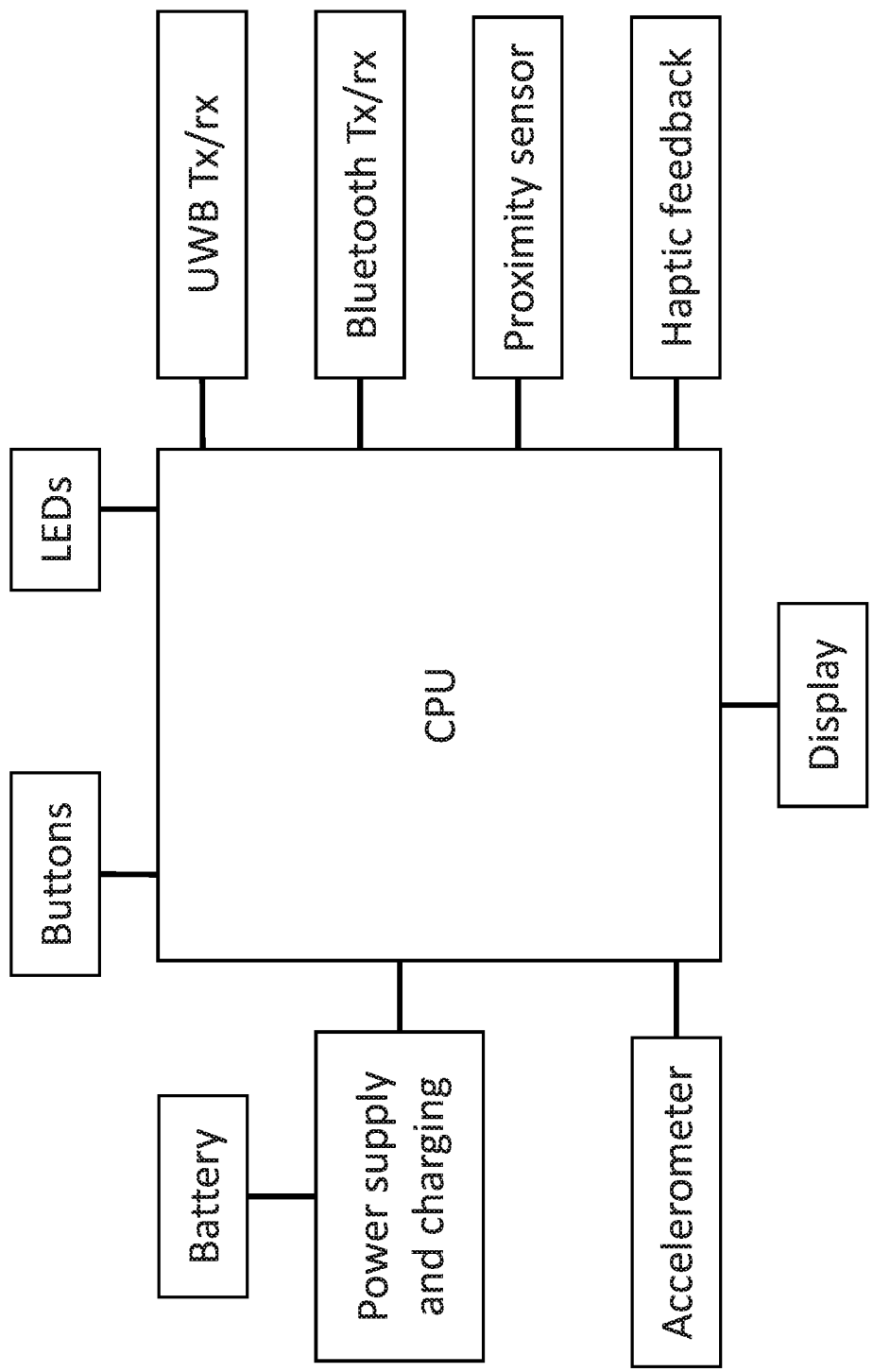
FIGS. 4-5, 7-8 are simplified functional block diagrams useful in understanding certain embodiments of the present invention.

FIG. 4 is a simplified block diagram of a wearable e.g. tag which may be used standalone or may be used to implement the wearable (tag) of FIG. 2; some (any subset of) or all of the following blocks may be provided:

panic and/or OK Button/s configured for: "Panic" alerting, and for "Dismiss potential call for emergency service as false alarm", respectively. The "panic button" may more generally comprise any input device operative to trigger a signal to the backend server if manipulated by the elder. Typically, upon deducing at least one distress situation, the backend server notifies the elder or senior of its deduction of the distress situation (e.g. asks "are you ok?") and, if the elder manipulates the input device and the input device responsively signals the server, the server cancels the distress situation, thereby to reduce false alarms without requiring a human operator to contact the elder.

Display/s configured to show time and date, and/or also notifications (e.g. "Are you OK? If so please press ok button to dismiss").

Haptic feedback configured to alert the senior of pending notifications on the display. The haptic feedback may for example comprise vibration generated by a mechanical actuator. Haptic feedback does not depend on the often degraded sense of hearing in the elderly population, and is sufficiently discrete as not to prevent embarrassment or disruption if activated in the presence of other individuals.

LEDs deployed for illuminating suitable components of the wearable (e.g. buttons, display).

UWB transceiver configured for determining location of the tag and for receiving/transmitting data communication to/from the backend (e.g. via the anchors).

Bluetooth transceiver (e.g. a commercially available device, preferably with low power requirements) configured for receiving/transmitting data communication to/from the backend (e.g. via the smartphone application or via the attached appliance of FIG. 8).

Accelerometer configured for determining distress based on abnormal acceleration values (compared to the senior past acceleration values in the context of location and/or time of day and/or day of week), and to determine the senior mobility level for dynamic blinking and to determine (e.g. in conjunction with the proximity sensor) whether or not the wearable is being worn by the senior since if not, the backend server of FIG. 2 may act to send reminders to the senior to don the wearable.

Proximity sensor which may include an infra-red LED and receiver operative to transmit pulses of infra-red light which bounce back from objects encountered, toward the infra-red receiver. Time elapsed between infra-red pulse transmission and reception is analyzed to yield distance of the encountered reflecting object from proximity sensor. The proximity sensor may be mounted on the back side of the wearable so the distance to the senior body (e.g. wrist) may be detected. Using the proximity sensor and the accelerometer the wearable is able to determine whether the wearable is being worn or whether it has been removed from the senior's body.

According to certain embodiments the tag (wearable) has dynamic blinking functionality in which UWB transmissions by the UWB transceiver, used for real time localization, have time intervals therebetween of variable length, corresponding to estimates of the senior's variable levels of mobility, thereby to conserve power allowing the tag to operate for longer without recharging, relative to a tag not having the dynamic adaptive blinking mode of operation.

Dynamic blinking includes any technique which employs an adaptive and/or variable blinking rate (variable interval between blink events e.g.) which according to certain embodiments may be adjusted to reduce tag battery power consumption. Each blink event comprises UWB transmission (to the senior's wearable) and optionally also reception (from the senior's wearable) by the tag (e.g. of FIG. 4) and subsequent (e.g. conventional) determination of tag position accordingly. When senior is estimated to be relatively static (low senior mobility level) the blinking rate (frequency of blink events) may be lower than when the senior is estimated to be moving (high senior mobility level).

Any suitable technology may be employed to generate estimates of senior mobility levels such as but not limited to:
a. legacy sensors: The elders' movements could be detected by legacy sensors available in home/business security applications, e.g. PIR (passive infra-red) sensors that detect rapid changes in infra-red radiation.
b. observing the amount of changes between consecutive tag position estimations e.g. between the tag position estimated using blink event n and the tag position estimated using blink event (n+1). For example, observing a sequence of measurements of time-stamped tag positions allows for computation of average senior velocity. The blinking rate could be adjusted according to the senior velocity e.g. higher blinking rate for higher velocity vs. lower linking rate for lower senior velocity. For example, for constant position sampling rate the average velocity calculated from previous N samples is: sum(i from 1 to N): (square_root((x[n−i]−x[n−i−1])^2+(y[n−i]−y[n−i−1])^2))/N
c. tag may discern changes in anchor properties (e.g. anchor receive power level). It is appreciated that significant changes in anchor signal levels, e.g. relative to a predetermined threshold level of normative change in anchor signal levels, indicate that the tag is moving since the tag's distance from some anchors is increasing whereas the tag's distance from other anchors is decreasing. Therefore, rate of change in signal power level may be used as an indication of the velocity the person is moving. Alternatively or in addition anchor/s may observe changes in the tag signal level to estimate the tag velocity
d. combinations of any of the above.

The estimated mobility level of the senior which determines her or his tag's blinking rate may for example be determined by the maximum of tag- and anchor-based estimations of her or his current mobility. The tag estimates the mobility level based on changes in signal level of the anchors and wearable accelerometer measurements. Typically, each tag computes the coefficient of variance or relative standard deviation of an anchor's signal level over a certain time interval, e.g. a few seconds such as 3 or 5 or 10 or 20 seconds. The tag also typically computes the coefficient of variance of each axis (X/Y/Z) of the wearable accelerometer measurements for a certain time duration, e.g. 10 seconds. The tag's estimated mobility level may be a combination e.g. average or weighted average or other central tendency of the coefficient of variances of the anchor signal level measurements and the accelerometer X/Y/Z axis acceleration measurements.

Anchors may estimate the senior's mobility level based on changes in signal level of the tag and on a computation of tag velocity. Anchors may compute the coefficient of variance or relative standard deviation of the tag signal level over a certain time interval, e.g. a few seconds such as 3 or 5 or 10 or 20 seconds. The anchors may compute a tag central velocity, or tag average velocity, e.g. based on averaging or otherwise combining Euclidean distances between consecutive measured tag coordinates (X,Y).

For example, for the following sequence of received signal level: 0.093, 0.175, 0.180, 0.354, 0.477, 0.520, 0.573, 0.600, 0.756, 0.927 the mobility level (based on coefficient of variance) is 0.576. As is apparent from the above example, typically, as the mobility level and/or velocity increases, the blink rate increases, whereas, as the mobility level and/or velocity decreases, the blink rate decreases.

According to certain embodiments at least one real time location subsystem e.g. the wearable's accelerometer monitors a (typically relative) location of at least one portion of an elder's body in real time and the server is operative to identify at least one behavior anomaly accordingly and to perform the at least one service accordingly.

According to certain embodiments at least one wearable device includes an input device e.g. button operative to signal the server if manipulated by the elder and wherein upon deducing at least one distress situation, the server notifies the elder of deduction of the distress situation and, if the elder manipulates the input device and the input device responsively signals the server, the server cancels the distress situation, thereby to reduce false alarms without requiring a human operator to contact the elder.

Figure 5:
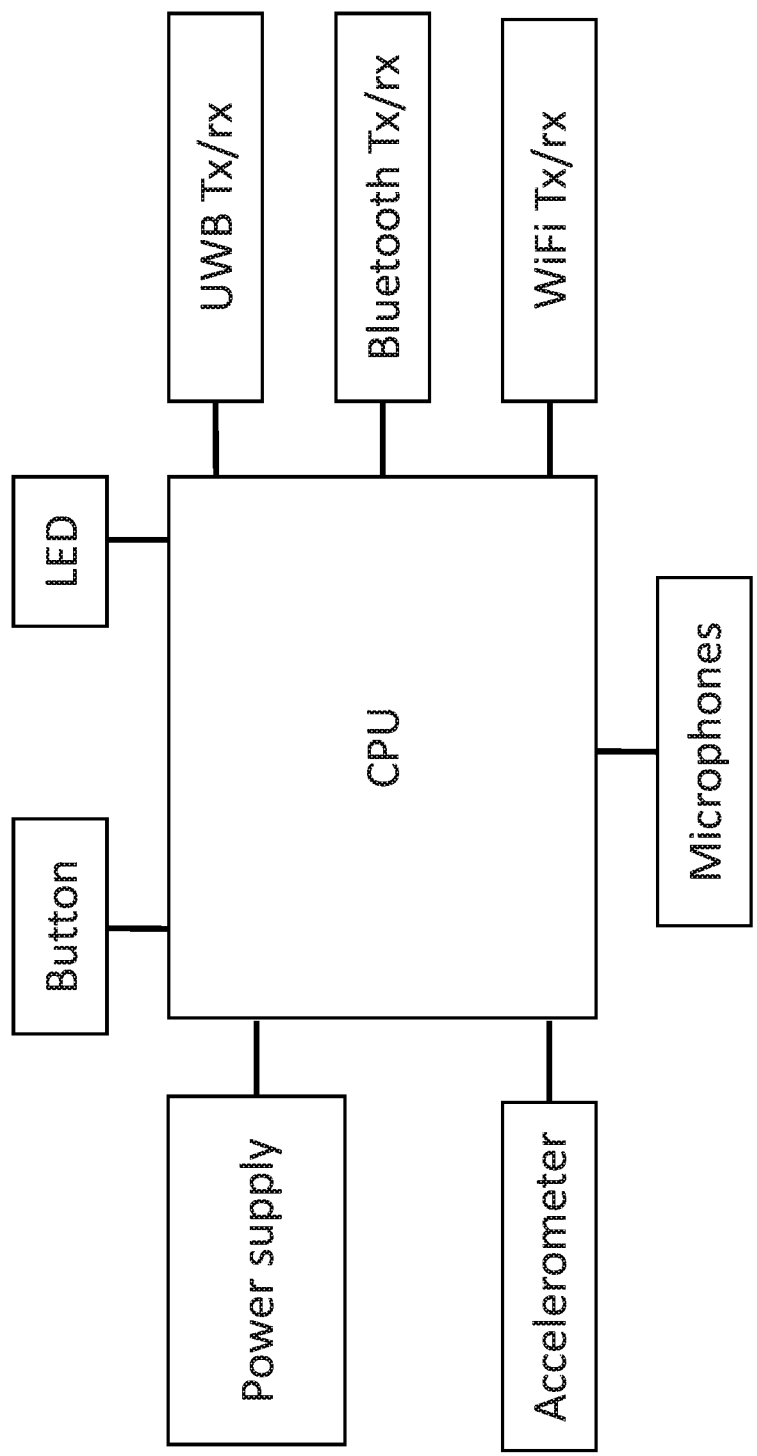

FIG. 5 is a simplified block diagram of an anchor which may be used standalone or may for example be used to implement the anchor of FIG. 2; some (any subset of) or all of the following blocks may be provided:

WiFi and Bluetooth transceivers (e.g. commercially available device/s, preferably with low power requirements);
Microphone/s configured to capture the senior voice;
UWB transceiver configured for determining location of the tag and for receiving/transmitting data communication to/from the tag and/or other anchors;
accelerometer configured to determine the orientation of the anchor in space for alignment of the angle yielded by AoA (angle-of-arrival) computations.

According to certain embodiments the anchor device is an angle-of-arrival based anchor device i.e. includes plural receiving elements and supports discernment of the wearable device's current angular orientation relative to the anchor device including computation of angles of arrival of incoming radio-frequency radiation received by the anchor device, by comparing arrival times of the incoming radiation at the receiving elements respectively.

Figure 6:
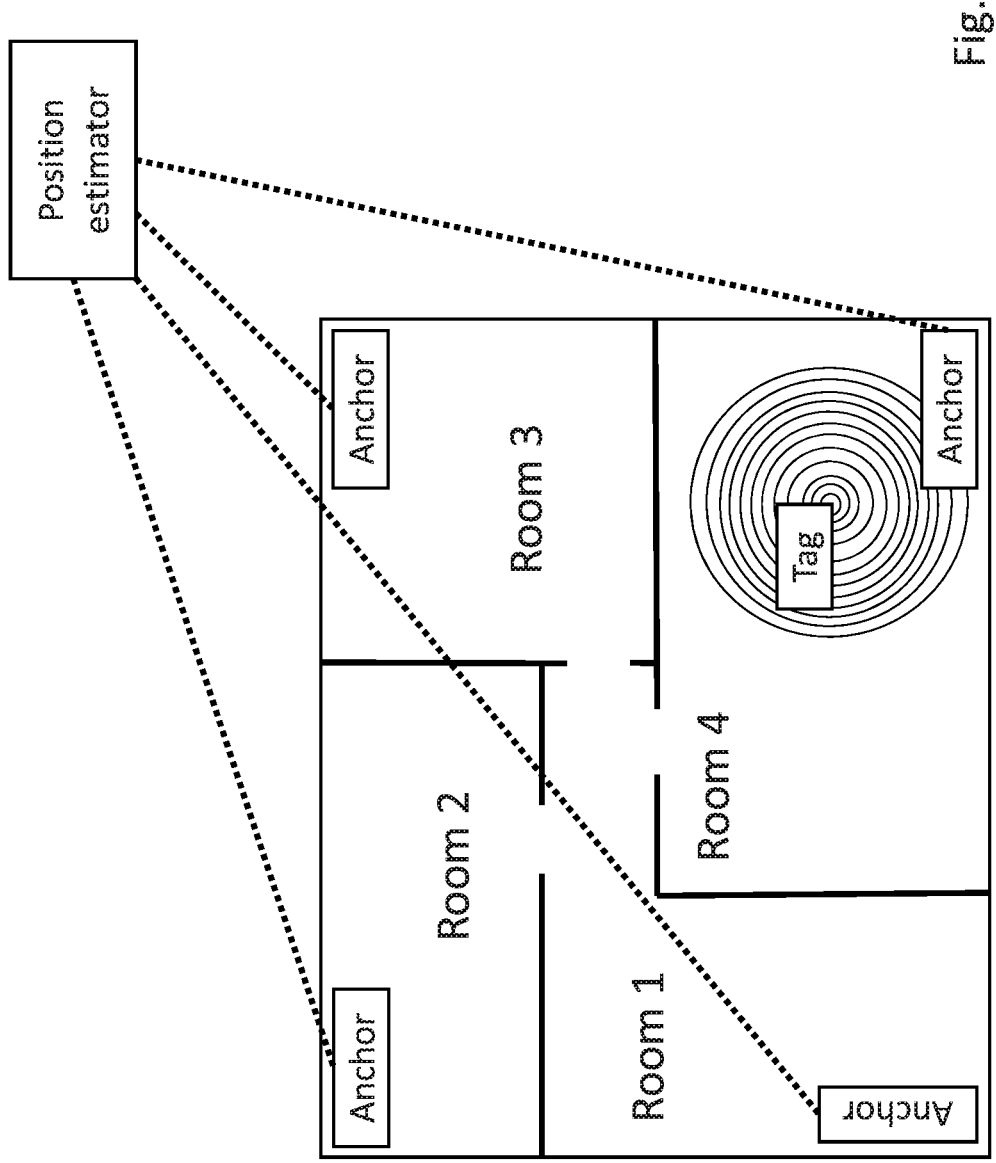
FIG. 6 is a simplified pictorial illustration of a senior's apartment in which anchors are deployed in accordance with certain embodiments of the present invention.

For example, FIG. 6 is a simplified pictorial illustration of a senior's apartment with no more than one anchor per room. A tag transmission is received by an AoA anchor. The uniform UWB signal radiated by the tag is received at different phases at different pulse peak times by the anchor receiving element. A position estimation entity, which may be wholly or partly implemented in software and may reside e.g. in the backend server or in a processor within the senior household collects the signal measurements from the anchors to determine the tag position. Due to use of AoA, a tag location may be determined using measurements from but a single anchor.

According to certain embodiments, anchors are permanently deployed in the senior's residence however these anchors' (permanent) locations within the residence are determined using "temporary anchors" which are deployed temporarily at the residence, used to achieve automatic topology discovery for calibration, and then removed e.g. by the technician who deploys the anchors in the course of his service visit and perhaps used by the same technician in a different residence belonging to another senior. Typically, the technician deploys "temporary anchors" which are sufficient in number to ensure that each anchor has a direct/clear line of sight (e.g. unobstructed by walls or furniture) to at least 3 additional anchors such that a first temporary anchor is localized at sub-meter accuracy using (say) triangulation, then at least one additional anchor is localized relative to that first anchor's known location, then other anchors are localized based on the at least one additional anchor's location as known by (say) triangulation, and so forth.

Figure 7:
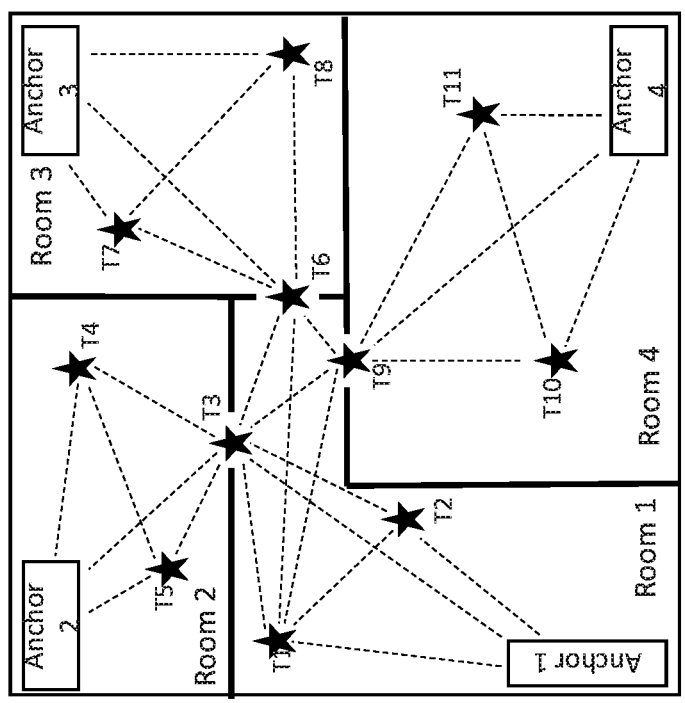

Temporary anchors may be placed on the floor or over furniture e.g. using tripods or in any other suitable location. The temporary anchors are typically placed in locations that ensure that there exists (at least one) permanent anchor designated the "root" (aka "master"), from which 3 (preferably, or 1 or 2) different paths exist to each other anchor. The paths could be multi-hop such that the paths include plural spans between permanent or temporal anchors. The 3 different multi-hop paths each typically include only clear-line-of-sight spans, and if at least one span within 2 multi-hop paths is different, that pair of paths is considered "different". The temporary anchors are typically removed after the position of each (permanent) anchor is computed (e.g. using conventional triangulation methods) and may be re-used when localizing the permanent anchors for another senior in the technician's next house call. A particular advantage is low-error computation of the position of each permanent anchor since the computation is based on the line-of-sight paths. Example: In FIG. 7, anchors 1 to 4 are permanent whereas anchors T1 to T11 are temporary. Spans i.e. direct or clear (unobstructed by furnishings etc.) lines-of-sight between anchors are indicated by dotted lines.

Since the location resolving functionality of the back-end server typically assumes that the anchors' positions are known, technicians who install anchors are often instructed to physically measure the installation point of each anchor (e.g. with the assistance of laser range meter). However automatic anchor topology discovery is advantageous e.g. if at least some, or all, anchors automatically determine their own positions relative to a "master" anchor without the technician needing to manually measure each anchor's location, thereby reducing length of the service call, inaccuracy of measurement e.g. due to walls and furniture introducing unknown levels of measurement error, and required technician skill level. The automatic anchor topology discovery may be used to measure distances and angles between each of some (any subset of) or all pairs of anchors deployed in the senior's residence; these distances and angles may then be used for real time localization of the senior including, if desired, use of Angle-of-Arrival technology e.g. as described herein or as is conventional.

According to certain embodiments, measurement error for several positions in the household is determined during set-up e.g. by a technician in the course of his service visit. For example, the technician may wear a tag (later intended to be worn by the senior) and may remain stationary, or may otherwise cause the tag to remain stationary within the coverage area of measurement of at least one anchor. Each anchor's determination of the tag's location is then recorded several times. The difference between the locations of the stationary tag as reported by the anchor, are indicative of the level of measurements errors characterizing the measured position in the household.

A particular advantage of certain embodiments is that sensors need not necessarily be deployed on "things" (objects in the senior's household); instead, suitable combinations of the apparatus and methods herein may be used to provide appropriate services to each senior, which greatly eases deployment since wearables, for example, do not incur any instalment costs.

During the same technician's service visit, a wi-fi network may be deployed in each senior's residence, if not already available, including a wireless network router and some (any subset of) or all of the terminal (e.g. tablet), anchor/s and attached appliance/s of FIG. 2. Any suitable solution may be used to provide a suitable residential WiFi network, such as but not limited to MiFi.

Generally, installations are done per senior and her or his apartment. Association of some system components (e.g. wearable, anchors, terminal) are done to a senior so emergency services are dispatched to the correct address when relevant distress is triggered. Learning/training of behavioral models are done per senior. An example for the per care center procedure is the workflow of handling distress.

FIG. 8 is a simplified block diagram illustration of an attachment appliance that may be mounted on footwear or clothes and may be provided standalone or may be used to implement the attachment appliance of FIG. 2.

Typically, when the elder is out-of-home, the subsystem of FIG. 8 provides wearable functionalities, since adding to the indoor wearable, hardware to support out-of-home communication and location capabilities would increase the wearable size and weight, and thus degrade user experience. On the other hand, the senior may not, or not always, carry a cellphone. Wearable functions provided by the apparatus of FIG. 8 may for example include some (any subset of) or all of the following:

Allow the Senior to indicate distress by pressing on panic button, and triggering response from emergency service provider functionality at the backend service provider;

Allow the senior to receive notifications from backend (e.g. Are you OK?); and

Determine senior location for dispatching emergency services.

The appliance of FIG. 8 may be attached to outerwear e.g. senior footwear (e.g. shoes) in any suitable manner such as but not limited to via a clip via adhesive, via locking pin(s) though the fabric/leather/rubber of the shoe, locking pin(s) though existing holes in the shoe, via fastening device/s e.g. wires or straps or Velcro fastening the appliance to the shoe or using exiting shoe detail like the shoe laces. Advantages or benefits of attaching the appliance of FIG. 8 to outerwear e.g. shoes include e.g. that shoes are less likely to be placed in a washing machine, that seniors may have less shoes than clothes, and that seniors with cognitive degradation are less likely to leave home without shoes than without any given article of clothing. The attachment appliance could be mounted on only one shoe out of a shoe pair. The attachment appliance could be removed from one shoe and mounted on a different shoe or pair of shoes.

The attachment appliance of FIG. 8 may include some (any subset of) or all of:

Battery (primly or rechargeable)
CPU with volatile and non-volatile memory
Bluetooth for communication with the wearable
Cellular transceiver for out-of-home communication and potentially location determination,
together with none, some (any subset of) or all of:
WiFi transceiver for out-of-home communication and potentially location determination
GNSS (e.g. GPS) for out-of-home location determination
accelerometer sensor e.g. for detection of shoe wearing. The apparatus of FIG. 8 may optimize battery use by remaining in a low power consumption mode unless and until senior movement is detected by the accelerometer sensor. Typically, once shoe movement is detected e.g. by the accelerometer, the appliance of FIG. 8 remains in its low power consumption mode but activates its Bluetooth transceiver. However, when the wearable connects to the attachment unit (e.g. when wearable detects senior is no longer in the residence) the attachment unit reverts from its low power mode into its normal operation mode.

Any suitable modes of interaction may be provided between the sub-system of FIG. 8 and the backend server of FIG. 2. For example, typically, the backend server is operative to notice that the senior has left residence without a shoe carrying attachment appliance e.g. by detecting absence of the wearable in the household in conjunction with failure of the paired shoe attachment device reporting movement. The backend server may then conclude that a new pair of shoes has been purchased which needs to be equipped with the attachment appliance of FIG. 8. The attachment appliance could report to backend on battery status for notifying need for recharging or battery replacement.

The optional button illustrated can be pressed (or replaced by operation any other input functionality) to cause the LED to blink to indicate battery charge level e.g. 5 blinks=fully charged, 1 blink=almost drained, no blink=battery fully depleted.

Improved wearable reception range is an advantage of certain embodiments described herein. Conventional indoor wearables with panic buttons often need WiFi or Bluetooth communication to a household hub but some household areas lack reliable coverage so an emergency event might fail to be relayed to the care giving organization operator. In contrast, ultra-wide-band transmission technology as employed herein has superior reception properties and may rely on multiple receiving elements (e.g. anchors) deployed in the household.

Distress detection with low latency and zero miss-detection ratio are advantages of certain embodiments described herein. Conventional location sensors often detect the location of a senior in her or his apartment with up to 3 m accuracy or require the senior to perform an action (e.g. open refrigerator door). Certain embodiments described herein may locate the senior with less than 50 cm accuracy which allows the senior's location to be compared to a previously stored location of an article of furniture, appliance or room e.g. to deduce that the senior is on a sofa or in the middle of a room.

The teachings of the presently disclosed subject matter are not limited to flows presented herein by description or otherwise; the operations can occur out of the order presented e.g. any pair of first and second operations may be performed substantially concurrently or in the reverse order. Whilst a flow chart may be described with reference to specific elements of the system, this is by no means binding, and the operations can be performed by elements other than those described herein.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Features of the present invention, including method steps, which are described in the context of separate embodiments may also be provided in combination in a single embodiment. Conversely, features of the invention, which are described for brevity in the context of a single embodiment or in a certain order may be provided separately or in any suitable subcombination or in a different order.

Those skilled in the art will readily appreciate that various modifications and changes can be applied to the embodiments of the invention as hereinbefore described without departing from its scope, defined in and by the appended claims.

The invention claimed is:

1. A client system for monitoring elders in a residential setting, the client system comprising:
   communication apparatus operative for sending real time localization data and elder body motion data toward at least one server configured for performing at least one elder-supporting backend service responsive to at least one of said real time localization data and elder body motion data; and
   at least one real-time location subsystem including:
   at least one wearable ("tag") including at least one ultra-wide-band (UWB) communication transceiver and an accelerometer sensing at least one body motion of an elder wearing the tag thereby to provide said elder body motion data; and
   at least one anchor device for deployment in an elder's domicile including an ultra-wide-band (UWB) communication transceiver operative for real time sub-meter localization of said tag, thereby to provide said real time localization data,
   wherein said backend service comprises generating at least one alarm upon detecting that the elder has been in a location L for a time period T, which is abnormal relative to a norm wherein the norm is generated by machine learning and wherein an individual behavioral model is learned per elder.

2. The system according to claim 1, wherein at least one real time location subsystem monitors an elder's location in real time and the server is operative to identify at least one location anomaly accordingly and to perform said at least one service accordingly.

3. The system according to claim 1, wherein at least one real time location subsystem monitors a location of at least one portion of an elder's body in real time and the server is operative to identify at least one behaviour anomaly accordingly and to perform said at least one service accordingly.

4. The system according to claim 1, wherein the server includes logic configured for receiving data from the at least one real time location subsystem and logically deducing at least one activity being performed by the elder's body and selecting at least one attribute of said at least one service accordingly.

5. The system according to claim 1, wherein the server includes logic configured for receiving data from the at least one real time location subsystem and logically deducing at least one distress situation and wherein said at least one service includes alerting emergency service providers responsive to said distress situation.

6. The system according to claim 1, wherein at least one wearable device includes an input device operative to signal the server if manipulated by the elder and wherein upon deducing at least one distress situation, the server notifies the elder of deduction of the distress situation and, if the elder manipulates the input device and the input device responsively signals the server, the server cancels the distress situation, thereby to reduce false alarms without requiring a human operator to contact the elder.

7. The system according to claim 1, wherein the at least one wearable device includes a first battery-operated device ("attachable appliance") having a cellular transceiver supporting outdoor communication and real time location and a second device which does not support outdoor communication and real time location.

8. The system according to claim 7, wherein the first device is configured to be mounted on an article of outerwear such as but not limited to a shoe.

9. The system according to claim 7, wherein each elder's first device includes communication functionality for communicating with the elder's second device.

10. The system according to claim 1, further and also comprising an elder's terminal including a CPU, memory, at least one input device and at least one output device.

11. The system according to claim 1, further comprising a cell app configured to serve at least one significant other, such as a family member, of the elder.

12. The system according to claim 1, further comprising a web client configured to serve at least one care-giving-organization end-user and wherein the elder-supporting backend service includes determining alerts, responsive to said data, requiring attention of a care-giving organization and sending said alerts to at least one care-giving organization and also comprising logic for cancelling alerts which the care-giving organization indicates, using said web client, to have been handled, logic sorting alerts not yet cancelled by urgency, and dashboard logic for displaying said alerts not yet cancelled in descending order of urgency.

13. The system according to claim 1, wherein the tag has dynamic adaptive blinking functionality in which UWB transmissions by the transceiver, used for real time localization, have time intervals therebetween of variable length, corresponding to estimates of the senior's variable levels of mobility, thereby to conserve power allowing the tag to operate for longer without recharging, relative to a tag not having the dynamic blinking mode of operation.

14. The system according to claim 1, wherein the anchor device comprises an angle-of-arrival based anchor device having plural receiving elements and supporting discernment of the wearable device's current angular orientation relative to the anchor device including computation of angles of arrival of incoming radio-frequency radiation received by the anchor device, by comparing arrival times of the incoming radiation at said receiving elements respectively.

15. The system according to claim 1, wherein the communication apparatus is operative for sending said real time localization data and elder body motion data toward at least one server operative for performing at least one elder-supporting backend service selected by comparing elder body motion data to a stored profile of elder body motion data characterizing an elder location indicated by said real time localization data.

16. The system according to claim 1, further comprising temporary anchor devices which support sub-meter localization of permanent locations of said at least one anchor device, for storage in the at least one server, when the temporary anchor devices are temporarily deployed such that:
said at least one anchor device includes only anchor devices having a path to a permanent anchor designated "root",
and such that at least one and preferably plural different paths exist from the root anchor to each other anchor.

17. The system according to claim 1, wherein said server and said client system are within a single residence and communicate via a LAN.

18. The system according to claim 1, wherein abnormality of at least one of the location L and time T are determined individually for individual elders, by comparing to an individual norm of times spent in various locations for that elder generated during an elder-specific learning/training stage.

19. The system according to claim 18, wherein said elder-specific learning/training stage includes generation of a heat map representative of an individual elder's movement in the house, indicating expected times the elder stays in specific locations in the elder's environment.

20. The system according to claim 1, wherein Z axis location information is used to enable the system to distinguish an elder lying on the ground from an elder who is standing or sitting.

21. The system according to claim 1, wherein Z Axis sensor fusion is provided between the UWB and a wearable Barometer to determine whether a worn sensor previously found to be above the floor has been detected at floor height.

22. A method for monitoring elders in a residential setting, the method comprising providing a client system, including:
providing communication apparatus operative for sending real time localization data and elder body motion data toward at least one server configured for performing at least one elder-supporting backend service responsive to at least one of said real time localization data and elder body motion data; and
providing at least one real-time location subsystem including:
at least one wearable ("tag") including at least one ultra-wide-band (UWB) communication transceiver and an accelerometer sensing at least one body motion of an elder wearing the tag thereby to provide said elder body motion data; and
at least one anchor device for deployment in an elder's domicile including an ultra-wide-band (UWB) communication transceiver operative for real time sub-meter localization of said tag, thereby to provide said real time localization data,
wherein said backend service comprises extraction of activities of daily living (adls) including at least one operation which employs machine learning based data analytics and wherein an individual behavioral model is learned per elder.

23. The method according to claim 22, further comprising alerting for possible distress based on sensing of senior voice data by said at least one anchor device and detection of predetermined phrases indicative of possible distress, within said senior voice data.

24. The method according to claim 22, wherein said at least one operation comprises sensor activation creating a sensor event.

25. The method according to claim 22, wherein said at least one operation comprises aggregation of a number of sensor events over some time period into a single ADL.

26. The method according to claim 22, wherein said at least one operation comprises aggregation of a number of sensor events over some time period into an indication of a distress situation pre-defined to trigger action.

27. The method according to claim 22, wherein said at least one operation comprises fusing a sequence of activities into a behavior pattern.

28. The method according to claim 22, wherein said at least one operation comprises detection of behavior pattern changes pre-defined to trigger action.

29. The method according to claim 22, wherein activity recognition is implemented by at least one of Hidden Markov Models and Conditional Random Fields.

30. A computer program product, comprising a non-transitory tangible computer readable medium having computer readable program code embodied therein, said computer readable program code adapted to be executed to implement a method for monitoring elders, said method comprising:
employing communication apparatus operative for sending real time localization data and elder body motion data toward at least one server configured for performing at least one elder-supporting backend service responsive to at least one of said real time localization data and elder body motion data; and employing at least one real-time location subsystem including:

at least one wearable ("tag") including at least one ultra-wide-band (UWB) communication transceiver and an accelerometer sensing at least one body motion of an elder wearing the tag thereby to provide said elder body motion data; and at least one anchor device for deployment in an elder's domicile including an ultra-wide-band (UWB) communication transceiver operative for real time sub-meter localization of said tag, thereby to provide said real time localization data, wherein upon deducing at least one distress situation, the server notifies the elder of deduction of the distress situation and wherein, following the elder manipulating an input device which is incorporated into said at least one wearable and which is operative to signal the server if manipulated by the elder, the server, responsive to the input device's having signaled the server, cancels the distress situation, thereby to reduce false alarms without requiring a human operator to contact the elder.

* * * * *